US010213523B2

(12) United States Patent
Ruberti et al.

(10) Patent No.: US 10,213,523 B2
(45) Date of Patent: Feb. 26, 2019

(54) MECHANOCHEMICAL COLLAGEN ASSEMBLY

(71) Applicant: Northeastern University, Boston, MA (US)

(72) Inventors: Jeffrey W. Ruberti, Lexington, MA (US); Jeffrey Paten, Boston, MA (US)

(73) Assignee: Northeastern University, Boston, MA (US)

( * ) Notice: Subject to any disclaimer, the term of this patent is extended or adjusted under 35 U.S.C. 154(b) by 481 days.

(21) Appl. No.: 14/763,860

(22) PCT Filed: Feb. 4, 2014

(86) PCT No.: PCT/US2014/014746
§ 371 (c)(1),
(2) Date: Jul. 28, 2015

(87) PCT Pub. No.: WO2014/121303
PCT Pub. Date: Aug. 7, 2014

(65) Prior Publication Data
US 2015/0359929 A1    Dec. 17, 2015

Related U.S. Application Data

(60) Provisional application No. 61/760,396, filed on Feb. 4, 2013.

(51) Int. Cl.
*A61L 27/24*     (2006.01)
*A61L 27/50*     (2006.01)
(Continued)

(52) U.S. Cl.
CPC .............. *A61L 27/24* (2013.01); *A61L 27/50* (2013.01); *B29C 55/00* (2013.01); *C07K 14/473* (2013.01); *C07K 14/78* (2013.01); *B29K 2089/00* (2013.01)

(58) Field of Classification Search
CPC ......... A61L 27/24; A61L 27/50; B29C 55/00; C07K 14/78; C07K 14/473; B29K 2089/00
(Continued)

(56) References Cited

U.S. PATENT DOCUMENTS 2,598,608 A * 5/1952 Salo .................. A61L 15/40
106/160.1
3,178,301 A * 4/1965 Veis ................... A22C 13/0016
106/156.2
(Continued)

FOREIGN PATENT DOCUMENTS

JP    2012519537 A    8/2012

OTHER PUBLICATIONS

Arden, N. and Nevitt, M. C., "Osteoarthritis: Epidemiology," Best Prac. Res. Clinc. Rheumatol., vol. 20, No. 1, pp. 3-25 (Feb. 2006).
(Continued)

*Primary Examiner* — Jeffrey M Wollschlager
(74) *Attorney, Agent, or Firm* — Arent Fox LLP

(57) ABSTRACT

Methods and devices are described for using a controlled extensional strain to organize prefibrillar collagen and/or elastin solutions into an organized array of fibrils. The organized array of collagen fibrils produced by the disclosed methods and devices can be used for tissue engineering applications.

13 Claims, 20 Drawing Sheets

(51) Int. Cl.
  *B29C 55/00* (2006.01)
  *C07K 14/47* (2006.01)
  *C07K 14/78* (2006.01)
(58) Field of Classification Search
  USPC .................................................... 264/202
  See application file for complete search history.

(56) References Cited

U.S. PATENT DOCUMENTS

| | | | | |
|---|---|---|---|---|
| 3,205,711 | A * | 9/1965 | Rano | G01N 30/12 422/89 |
| 4,544,516 | A * | 10/1985 | Hughes | A61L 27/24 128/DIG. 8 |
| 4,643,309 | A * | 2/1987 | Evers | A61J 1/2096 206/364 |
| 4,686,962 | A * | 8/1987 | Haber | A61F 2/004 128/DIG. 25 |
| 5,356,406 | A * | 10/1994 | Schraga | A61J 1/2096 215/DIG. 3 |
| 5,378,469 | A * | 1/1995 | Kemp | A61L 27/24 264/178 R |
| 5,475,052 | A * | 12/1995 | Rhee | A61L 15/225 523/113 |
| 5,718,012 | A * | 2/1998 | Cavallaro | A61L 27/24 8/127.5 |
| 5,997,896 | A * | 12/1999 | Carr, Jr. | A61L 27/24 424/426 |
| 6,565,960 | B2 * | 5/2003 | Koob | C08H 1/06 428/297.4 |
| 6,592,794 | B1 * | 7/2003 | Bachrach | D01F 4/00 264/178 F |
| 7,048,963 | B2 * | 5/2006 | Braithwaite | A61L 27/24 427/2.24 |
| 7,338,517 | B2 * | 3/2008 | Yost | B29C 47/0023 424/423 |
| 8,338,570 | B2 * | 12/2012 | Saeidi | C08H 1/06 530/356 |
| 8,492,332 | B2 * | 7/2013 | Paukshto | A61L 27/24 514/7.2 |
| 8,648,144 | B2 * | 2/2014 | Hadba | A61L 27/34 264/176.1 |
| 8,986,378 | B2 * | 3/2015 | Koob | A61F 2/02 623/13.11 |
| 9,018,355 | B2 * | 4/2015 | Saeidi | C08H 1/06 530/356 |
| 9,101,681 | B2 * | 8/2015 | Hassingboe | A61L 15/32 |
| 9,394,627 | B2 * | 7/2016 | Peno | D01D 5/18 |
| 9,518,106 | B2 * | 12/2016 | Saeidi | C08H 1/06 |
| 9,603,968 | B2 * | 3/2017 | Koob | A61L 27/24 |
| 2004/0110439 | A1 * | 6/2004 | Chaikof | A61L 15/32 442/123 |
| 2005/0258562 | A1 * | 11/2005 | Wilson | D01D 1/065 264/130 |
| 2006/0178626 | A1 * | 8/2006 | Axelsson | A61M 5/322 604/110 |
| 2007/0269476 | A1 * | 11/2007 | Voytik-Harbin | A61L 27/24 424/422 |
| 2009/0131879 | A1 * | 5/2009 | Lu | A61M 5/322 604/240 |
| 2010/0227043 | A1 | 9/2010 | Fuller et al. | |
| 2011/0166325 | A1 * | 7/2011 | Saeidi | C08H 1/06 530/356 |
| 2012/0021217 | A1 * | 1/2012 | Hadba | A61L 17/04 428/375 |
| 2012/0027732 | A1 * | 2/2012 | Voytik-Harbin | A61L 27/24 424/93.7 |
| 2012/0273993 | A1 * | 11/2012 | Shoseyov | A61L 27/24 264/202 |
| 2013/0023648 | A1 * | 1/2013 | Wnek | C07K 1/107 530/356 |
| 2015/0182660 | A1 * | 7/2015 | Nazhat | A61L 27/24 424/93.7 |

OTHER PUBLICATIONS

Bailey, A. J. and Rhodes, D. N., "Irradiation-Induced Crosslinking of Collagen," Radiation Research, vol. 22, pp. 606-621 (Aug. 1964).
Bischoff White, E. E., et al., "Extensional-flow-induced crystallization of isotactic polypropylene," Rheologica Acta, vol. 51, No. 4, pp. 303-314 (Apr. 2012).
Caves, J. M., et al., "Fibrillogenesis in Continuously Spun Synthetic Collagen Fiber," J. Biomed. Maters. Res. B Appl. Biomater., vol. 93, No. 1, 31 pages (Apr. 2010).
Chellamuthu, M., "Extensional flow-induced crystallization of isotactic poly-1-butene using a filament stretching rheometer," J. Rheol., vol. 55, No. 4, pp. 901-920 (Jul./Aug. 2011).
Cowin, S. C., "Do liquid crystal-like flow processes occur in the supramolecular assembly of biological tissues?" Journal of Non-Newtonian Fluid Mechanics, vol. 119, No. 1-3, pp. 155-162 (May 1, 2004).
Cowin, S. C., "How is a Tissue Built?" Journal of Biomechanical Engineering, vol. 122, No. 6, pp. 553-569 (Dec. 2000).
Housley, T. and Tanzer, M. L., "Collagen crosslinking: Isolation of hydroxyaldol-histidine, a naturally-occurring crosslink," Biochemical and Biophysical Research Communication, vol. 67, No. 2, pp. 824-830 (Nov. 17, 1975).
International Search Report and Written Opinion issued by the U.S. Patent and Trademark Office as International Searching Authority for International Application No. PCT/US14/14746 dated Apr. 17, 2014 (10 pages).
Katz, J. N., "Lumbar Disc Disorders and Low-Back Pain: Socioeconomic Factors and Consequences," The Journal of Bone & Joint Surgery, Supplemental 2, pp. 21-24 (Apr. 2006).
Lyman, S., et al., "Epidemiology of Anterior Cruciate Ligament Reconstruction. Trends, Readmissions, and Subsequent Knee Surgery," The Journal of Bone & Joint Surgery, vol. 91-A, pp. 2321-2328 (2009).
Mechanic, G. and Tanzer, M. L., "Biochemistry of collagen crosslinking. Isolation of a new crosslink, hydroxylysinohydroxynorleucine, and its reduced precursor, dihydroxynorleucine, from bovine tendon," Biochemical and Biophysical Research Communications, vol. 41, No. 6, pp. 1597-1604 (Dec. 24, 1970).
Mechanic, G., et al., "The nature of crosslinking in collagens from mineralized tissues," Biochemical and Biophysical Research Communications, vol. 45, No. 3, pp. 644-653 (Nov. 5, 1971).
Nagda, S. H., et al., "Cost Analysis of Outpatient Anterior Cruciate Ligament Reconstruction," Clin. Orthop. Relat. Res., vol. 468, No. 5, pp. 1418-1422 (2010).
Oliveira, M. S. N., et al., "Viscous flow through microfabricated hyperbolic contractions," Experiments in Fluids, vol. 43, No. 2, pp. 437-451 (Aug. 2007).
Pipe, C. J. and McKinley, G. H., "Microfluidic rheometry," Mechanics Research Communications, vol. 36, No. 1, pp. 1-37 (Aug. 21, 2008).
Rothstein, J. P. and McKinley, G. H., "A comparison of the stress and birefringence growth of dilute, semi-dilute and concentrated polymer solutions in uniaxial extensional flows," Journal of Non-Newtonian Fluid Mechanics, vol. 108, pp. 275-290 (2002).
Rothstein, J. P. and McKinley, G. H., "Extensional flow of a polystyrene Boger fluid through a 4 : 1 : 4 axisymmetric contraction/expansion," Journal of Non-Newtonian Fluid Mechanics, vol. 86, No. 1-2, pp. 61-88 (Sep. 15, 1999).
Rothstein, J. P. and McKinley, G. H., "Inhomogeneous transient uniaxial extensional rheometry," J. Rheol., vol. 46, No. 6, pp. 1419-1443 (Nov./Dec. 2002).
Rothstein, J. P. and McKinley, G. H., "The axisymmetric contraction-expansion: the role of extensional rheology on vortex growth dynamics and the enhanced pressure drop," The Journal of Non-Newtonian Fluid Mechanics, vol. 98, pp. 33-63 (2001).
Rothstein, J. P., "Transient extensional rheology of wormlike micelle solutions," J. Rheol., vol. 47, No. 5, pp. 1227-1247 (Sep./Oct. 2003).
Ruberti, J. W. and Hallab, N. J., "Strain-controlled enzymatic cleavage of collagen in loaded matrix," Biochemical and Biophysical Research Communications, vol. 336, No. 2, pp. 483-489 (Oct. 21, 2005).

(56) References Cited

OTHER PUBLICATIONS

Saeidi, N., et al., "Dynamic shear-influenced collagen self-assembly," Biomaterials, vol. 30, pp. 6581-6592 (Sep. 17, 2009).
Shoshan, S. and Finkelstein, S., "Studies on collagen crosslinking in vivo," Biochimica et Biophysica Acta—Protein Structure, vol. 154, No. 1, pp. 261-263 (Jan. 22, 1968).
Siegel, R. C., "Biosynthesis of Collagen Crosslinks: Increased Activity of Purified Lysyl Oxidase with Reconstituted Collagen Fibrils," PNAS, vol. 71, No. 12, pp. 4826-4830 (Dec. 1974).
Swartz, M. A. and Fleury, M. E., "Interstitial Flow and Its Effects in Soft Tissues," Annu. Rev. Biomed. Eng., vol. 9, pp. 229-256 (Apr. 2007).
B. Lanfer, et al., "Aligned fibrillar collagen matrices obtained by shear flow deposition", Biomaterials, (2008), vol. 29, pp. 3888-3895.
M. K. Mulligan, et al., "The effect of confinement-induced shear on drop deformation and breakup in microfluidic extensional flows", Physics of Fluids, (2011), vol. 23, pp. 022004-1-022004-11.

* cited by examiner

First Iteration Chamber Design

A

Dr. Jonathan Rothstein,
University of Massachusetts - Amherst

B

2D-Symmetric Contractor Device

-1 (pure rotation)  0 (shear)  1 (pure elongation)

A

B

A

B

A

B

A

B

MECHANOCHEMICAL COLLAGEN ASSEMBLY

CROSS-REFERENCE TO RELATED APPLICATIONS

This application is the national stage entry of International Application No. PCT/US2014/014746, filed Feb. 4, 2014, which claims the benefit of U.S. Provisional Application No. 61/760,396, filed Feb. 4, 2013, the entire contents of which are hereby incorporated by reference in their entirety.

STATEMENT REGARDING FEDERALLY SPONSORED RESEARCH OR DEVELOPMENT

This invention was made with government support under Grant No. NEI EY015500 awarded by the National Institutes of Health. The government has certain rights in the invention.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

The disclosure is in the field of tissue engineering and medicine.

Collagen is present in many organisms. Collagen has evolved as the premier, load-bearing molecule in vertebrates and is responsible for sustaining tremendous forces within the human musculoskeletal system. Collagen is also the structural molecule of choice in a variety of other specialized connective tissues including blood vessels, cornea, fascia, periosteum sclera and skin. Unfortunately, when collagenous tissues fail and then fail to repair, the results can drastically affect patient mobility, increase the severity of other pre-existing conditions and ultimately, shorten life expectancy. Though significant effort has been expended to "tissue-engineer" natural grafts to replace damaged or diseased load-bearing extracellular matrices (ECMs) such as ligament, tendon and cornea, no clinically viable constructs have been produced. We currently have limited methods to repair or replace compromised, load-bearing collagenous tissues. Very little is known about the mechanisms which govern the organization and morphology of collagen during synthesis by fibroblasts in vivo, for it is the loss of or damage to organized collagen that is often irreparable. For example, the inability to reproduce collagenous structures de novo is attributable to a poor understanding of how fibroblastic cells control connective tissue production (Cowin, S. C., J Biomech Eng, 2000. 122(6): p. 553-69; Cowin, S. C., J. of Non-Newtonian Fluid Mechanics, 2004. 119(1-3): p. 155-162). Without a model from which to draw insight about control of collagen fibrillogenesis in vivo, tissue engineers rely heavily on seeded cells to direct the production of matrix, with limited success.

The fibril forming collagens in vertebrates (type I, II, III, V, XI) are the primary proteins responsible for bearing loads in blood vessel, bone, cartilage, cornea, intervertebral disk, ligament, sclera, skin and tendon. Degeneration of or damage to collagenous load-bearing structures continues to significantly diminish the quality of life of millions of individuals. Intervertebral disc degeneration can lead to lower back pain, which costs the United States more than $100 billion dollars per year. (Nagda, et al., Clin Orthop Relat Res, 2010. 468(5): p. 1418-22; Katz, J. N., J Bone Joint Surg Am, 2006. 88 Suppl 2: p. 21-4). There are as many as 175,000 ACL repairs performed annually in the U.S. at an estimated cost of 0.5 to 1.0 billion dollars. (Lyman et al., J Bone Joint Surg Am, 2009. 91(10): p. 2321-8). Collagen degradation in cartilage secondary to osteoarthritis will adversely affect the lives of more than 80% of Americans over 75 years of age and more than half of Americans over 60. (Arden, N. and M. C. Nevitt, Best Pract Res Clin Rheumatol, 2006. 20(1): p. 3-25). Tendon ruptures, aortic aneurysms, and keratoconus in the cornea are ultimately due to collagen network failures. There are also many collagen-related diseases due to genetic mutations, including Ehlers-Danlos syndrome, Bethlem myopathy, Alport syndrome, Knobloch syndrome, osteoporosis (some cases), osteogenesis imperfecta, arterial aneurysm and rheumatoid arthritis (autoimmune). For all of these conditions, there are few satisfactory treatments.

SUMMARY

This disclosure is based, at least in part, on the discovery that applying a controlled extensional strain and shear strain to a prefibrillar structural protein solution can induce the prefibrillar solution to organize into an array of fibrils. In some embodiments, a high extensional strain and low shear strain is applied to generate the organized array of fibrils, including collagen and elastin fibrils. Methods and devices for organizing the prefibrillar solution into an organized array of fibrils are disclosed.

In some aspects, methods of organizing prefibrillar solution into an organized array of fibrils are disclosed. The methods include providing a collagen and/or elastin solution, wherein the collagen and/or elastin are prefibrils; and creating a fluid flow through the prefibrillar solution to produce a controlled extensional strain and shear strain to the collagen and/or elastin prefibrils. In some embodiments, the extensional and shear strain are sufficient to induce the prefibrils to assemble into an organized array of fibrils. In some embodiments, the extensional strain is high, and the shear strain is low. In some embodiments, the solution further includes fibronectin and/or proteoglycans.

In some embodiments, a drawing probe is used to generate the extensional strain. In some embodiments, the solution is in the form of a droplet, sheet, sphere, or cylinder. In some embodiments, the methods include adding supplemental monomers to the solution during application of the tension. In some embodiments, the solution includes continuously extending a collagen and/or elastin fibrillar structure at various rates, including a rate of about 1 µm/second to about 1 mm/second. In some embodiments, the methods further include extending the collagen and/or elastin fibrillar structure in the presence of a co-nonsolvency agent.

In some embodiments, the methods include exposing the organized array of collagen and/or elastin fibrils to a solution that promotes recrystallization. In some embodiments, the solution is a buffer solution that includes a hypertonic agent. In some embodiments, the hypertonic agent is polyethylene glycol, hyaluronic acid, or glycosaminoglycans.

In some embodiments, the methods include applying tension to the organized array of fibrils as the fibrils recrystallize. In some embodiments, the concentration of the prefibrillar solution is about 1.2 mg/ml to about 500 mg/ml.

In some embodiments, the concentration of the prefibrillar solution is about 2.4 mg/ml to about 100 mg/ml.

In some aspects, a microfluidics device is disclosed. The devices includes a channel on or within the device comprising at least one inlet and at least one outlet. In some embodiments, a first microfluidic inlet on the structure is configured to transport a collagen and/or elastin solution at a controlled flow rate, and the collagen and/or elastin are prefibrils. In some embodiments, each of the at least one inlets is configured to merge into the channel that connects to the at least one outlet, and the controlled flow rate produces an extensional and shear strain that are sufficient to induce the prefibrils to assemble into an organized array of fibrils. In some embodiments, the extensional strain is high, and the shear strain is low.

In some embodiments, the microfluidic device is a flat structure or a cylindrical structure. In some embodiments, the microfluidics device includes a second microfluidic inlet on or within the structure that is configured to transport a biocompatible, immiscible fluid along inner walls of the channel. In some embodiments, the biocompatible, immiscible fluid is silicone oil or perfluorodecalin. In some embodiments, the fluid has low shear viscosity. In some embodiments, the device further comprises a third microfluidic inlet on the structure that is configured to transport a fluid that neutralizes and concentrates the collagen and/or elastin solution along inner walls of the channel and over the second fluid layer.

In some embodiments, the fluid that neutralizes and concentrates the collagen and/or elastin solution comprises polyethylene glycol, hyaluronic acid, or glycosaminoglycans. In some embodiments, the device is configured to control extensional strain-rate. In some embodiments, the channel near an end of the at least one inlet has a decreasing diameter compared to near an end of the at least one outlet, wherein the decreasing diameter of the channels allows control of the extensional strain and shear strain rates. In some embodiments, the pH, ionic strength, and/or concentration of the fibrillar solution is adjustable in the disclosed devices. In some embodiments, the concentration of the collagen and/or elastin prefibrillar solution is about 1.2 mg/ml to about 500 mg/ml. In some embodiments, the concentration of the collagen and/or elastin prefibrillar solution is about 2.4 mg/ml to about 100 mg/ml. In some embodiments, the solution further includes fibronectin and/or proteoglycans.

In some aspects, a method of using a microfluidics device includes providing a collagen and/or elastin solution to the first microfluidic inlet channel, wherein the collagen and/or elastin are prefibrils. The method includes creating a fluid flow through the prefibrillar solution that produces a controlled extensional strain and shear strain to the collagen and/or elastin prefibrils to assemble into an organized array of collagen and/or elastin fibrils. The method further includes collecting the organized array of collagen fibrils. In some embodiments, the method further includes collecting the organized array of collagen and/or elastin fibrils using an instrument that collects the fibrils at a rate equal to or faster than the flow rate of the solutions. In some embodiments, the instrument is a spool.

These and other aspects and embodiments of the disclosure are illustrated and described below.

BRIEF DESCRIPTION OF THE FIGURES

The foregoing and other objects of the present invention, the various features thereof, as well as the invention itself, may be more fully understood from the following description, when read together with the accompanying drawings. The drawings are presented for the purpose of illustration only and are not intended to limit the invention.

FIG. 4C is a representation of SEM micrograph that shows a disorganized collagen fibril structure produced without applying extensional strain.

FIG. 5B is a magnified representation of FIG. 5A.

DETAILED DESCRIPTION

Figure 1:
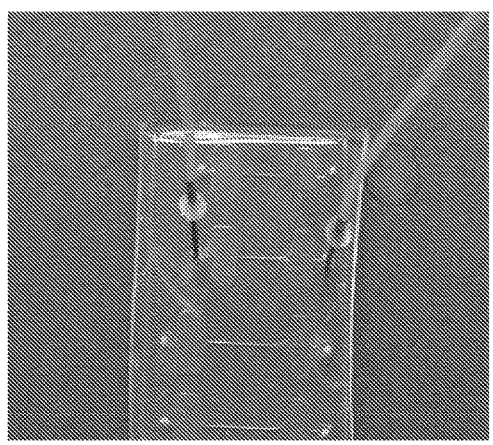
FIG. 1 is a representation of a microfluidic device according to some embodiments of the disclosure.
Figure 1:
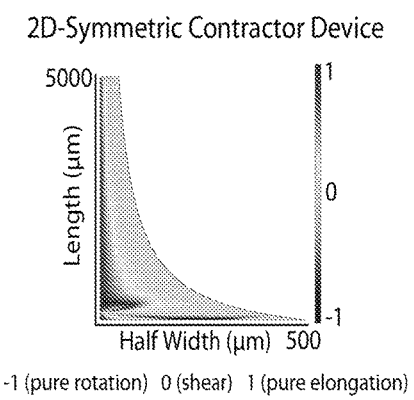

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs.

Definitions

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, a "fibril" is an aggregation of monomers, dimers, oligomers, and microfibrils that form into a continuous structure that appears fibrous with suitable magnification. A fibril is more than about 20 nm in diameter. In some embodiments, a fibril has variable length, ranging from 1 µm to about 20 µm, to millimeters and centimeters long.

As used herein, a "prefibrillar" solution refers to a solution containing monomers, dimers, trimers, oligomers, and microfibrils that that have not formed a continuous structure as that found in fibrils and fibers/fibrillar arrays. A "prefibril" is a molecular unit with a diameter less than about 20 nm in diameter and of variable length. Fibrils aggregate to form fibers, and the terms "fibers" and "fibrillar arrays" are used interchangeably. The terms "polymerization" and "crystallization" are used interchangeably, and refer to when a "prefibril" assembles into fibrils and/or fibers.

As used herein, "collagen" means a protein component of an extracellular matrix having a tertiary structure that includes polypeptide chains intertwining to form a collagen triple helix or having a characteristic amino acid composition comprising Gly-X-Y repeat units, or a fragment thereof. Collagens can be any collagen known in the art (e.g., one of collagen Type 1-29, including but not limited to I, II, III, IV, V, and XI). As described herein, in some embodiments, collagen is a principal component in a cooperative engineering material system, and this system significantly enhances the ability of fibroblastic cells to produce and optimize load-bearing tissue.

General

The methods described herein can be used to produce an organized array of fibrils, including collagen and/or elastin fibrils. The methods and systems described herein are based, at least in part, on the discovery that extensional strain can be used to assemble prefibril structural proteins to generate organized arrays of fibrils. In some aspects, the disclosed methods and devices take advantage of the strain-induced polymerization concept. In some embodiments, the solution/air interface is used to concentrate the prefibril and to generate mechanical strain to induce polymerization. For example, the fiber drawing methods described herein produce the most aligned collagenous structures seen in a laboratory to date. In some embodiments, microfluidic devices are used to apply a controlled extensional strain to generate an organized array of fibrils.

Figure 18:
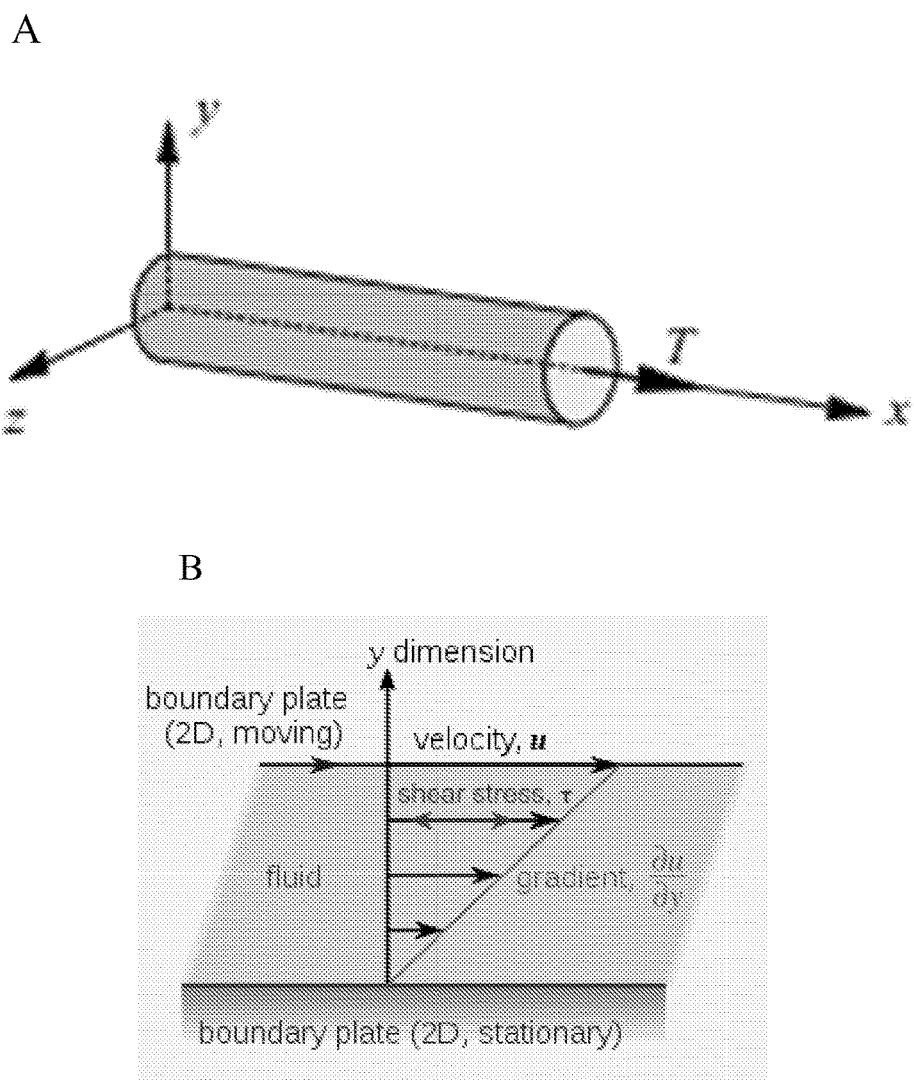
FIG. 18 is a schematic to illustrate the frame of reference for extensional strain.

Extensional strain (also known as normal or dimensional strain) measures changes in length along a specific direction or axis. In the disclosed methods and devices, extensional strain is not limited to uniaxial extensional strain. Any application of force that produces an elongational flow in any direction (for example, an equiaxial stretch of a planar sheet or inflation of a spherical shell) is contemplated in this disclosure. In some embodiments, extensional strain is a condition under which flow is created in a prefibrillar collagen solution that is dominated in at least one direction by a positive spatial derivative in the velocity along the dependent variable direction. To illustrate the concept, FIG. 18A provides a frame of reference for the x, y, and z axes, and T is the tension applied. A positive du/dx indicates that the u, which is the velocity in the x direction, is increasing with x.

Figure 12:
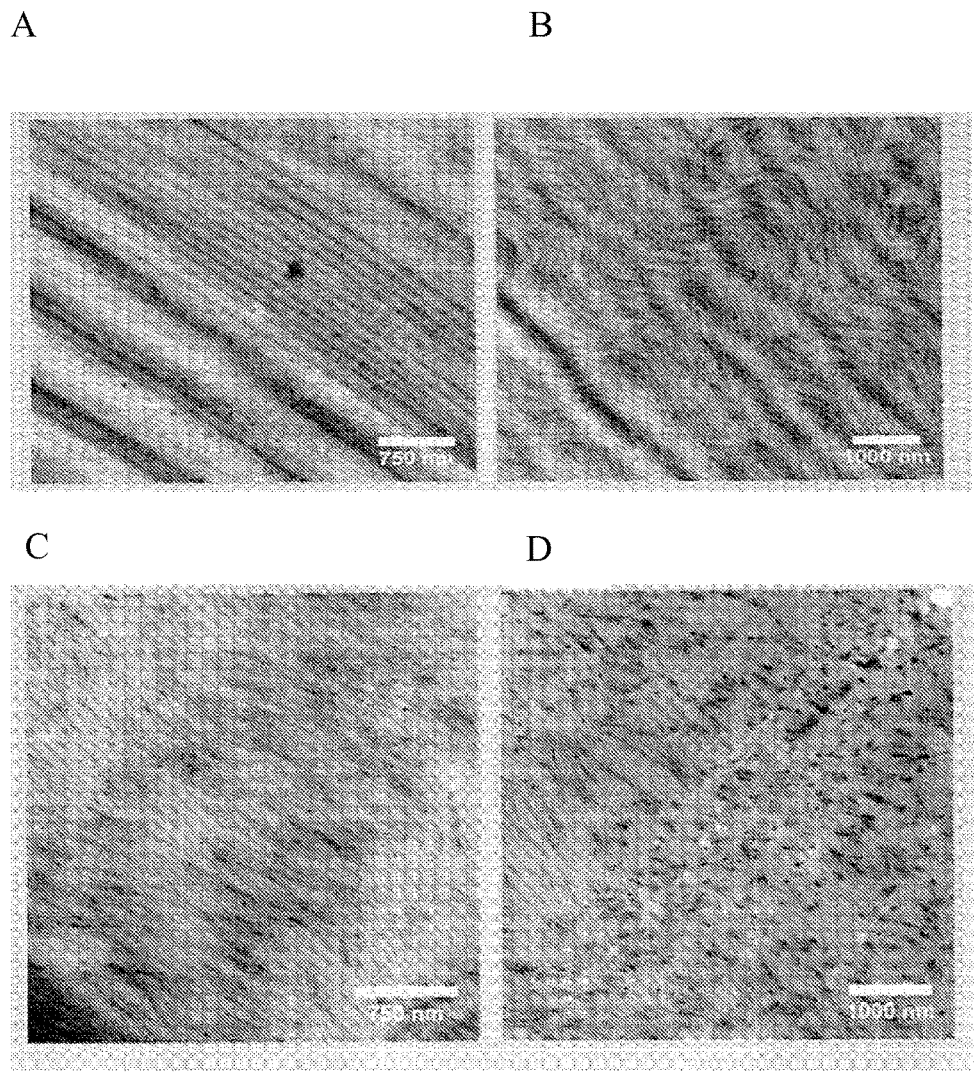
FIGS. 12A-D are representations of TEM images showing fibril formation using embodiments of the disclosed methods.

In some embodiments, a fluid flow with a high extensional strain rate that is suitable for producing organized collagen arrays requires a low shear rate. FIG. 18B provides a frame of reference for the x and y axes. Shear strain measures changes in angles with respect to two specific directions in response to shear stress. When shear strains are zero or near zero, angles are preserved. To define shear strains, one can consider two directions that form the plane that undergoes shear distortion. In some embodiments, low shear is achieved at a low or near zero value of du/dx. As illustrated in FIG. 18B, the velocity in the x direction (that is, u) should not change much with y-position. Otherwise, in some embodiments, when shear strain is too high, the method produces a disorganizing rotation. In other embodiments, some rotational flow or shear strain is included to "tune" the level of fibril organization. For example, in FIG. 12A-D are representations of TEM images showing fibril formation using embodiments of the disclosed methods, where the fibrils were rehydrated in phosphate buffered saline (PBS). FIG. 12A shows highly aligned fibrillar structure. FIG. 12B shows crimp patterns of smaller fibrils. FIG. 12C shows smaller fibrils beginning to coalesce, and FIG. 12D shows areas of disorganization. Thus, FIG. 12B is an example in which rotational flow or shear strain can be controlled to produce fibrils, for example, with "crimped" organization, which can mimic certain natural tissues. It is believed that the disorganization reflects the different flow rates during polymerization.

In some embodiments, extensional strain can be applied to a prefibrillar solution by contacting a microneedle to a droplet of the prefibrillar solution and withdrawing the microneedle. FIG. 12A is a schematic illustration of generating a collagen fibril from a droplet of prefibrillar collagen solution. A droplet of prefibrillar collagen solution was suspended from a column support, such as small metal needle, and a glass micro needle was used for drawing the fibril. The microneedle is contacted with the droplet and slowly withdrawn, creating a necking region, pulling collagen-containing liquid from the droplet as it moves and creating orienting forces along the direction of withdrawal. The prefibrillar collagen components of the solution align along the orienting forces and assemble into fibrils. In some embodiments, the drawing rate of the needle can provide the extensional strain. In some embodiments, the drawing rates are in the range of about 0.01 micrometer/second to about 1 meter/second. In other embodiments, the drawing rates are in the range of about 1 micrometer/second to about 1 cm/second. During the drawing of the fibril, the temperature, ionic strength, pH and buffers in the solution are all adjustable parameters.

Figure 2:
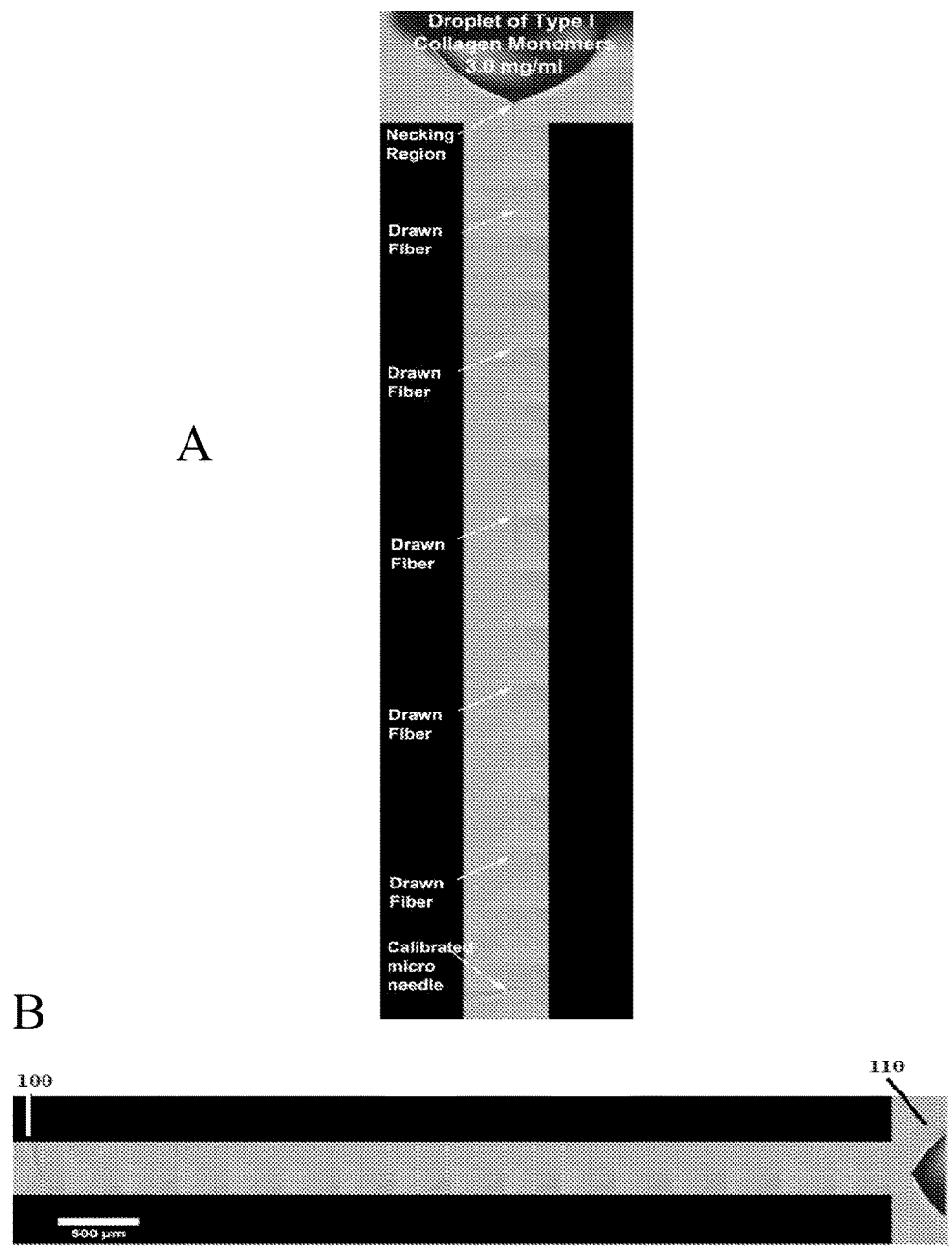
FIGS. 2A-B is a representation showing that a thin collagen fiber that was pulled directly from a droplet of prefibrillar collagen solution according to some embodiments.

FIGS. 2A-B and FIGS. 3A-B, described in more detail herein, shows representations of a thin collagen fiber that was pulled directly from a droplet containing prefibrillar collagen solution according to some embodiments. FIGS. 2A-B and FIGS. 2A-B show a necking region, which is the location where the collagen fiber is generated. The necking region generates a high extensional strain rate with a low shear rate as the collagen fiber exits the region, which generates a highly organized array of collagen fibrils. The waiting time was about five minutes, which ensured that the fibrillar solution had not polymerized before the fiber was pulled from the droplet. In some aspects, as discussed in more detail herein, the prefibrillar solutions are kept acidic and neutralized with a co-flow solution in the microfluidics methods to ensure that the solution has not polymerized before the fibrils are generated, which would result in disorganized arrays of fibers.

Figure 17:
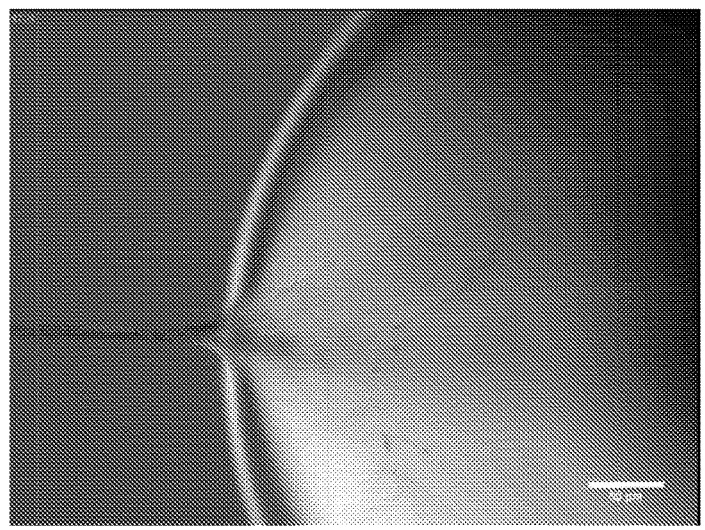
FIGS. 17A-B are representations of DIC images showing highly entangled, greatly disorganized fibrils that were not generated using the disclosed methods.
Figure 17:
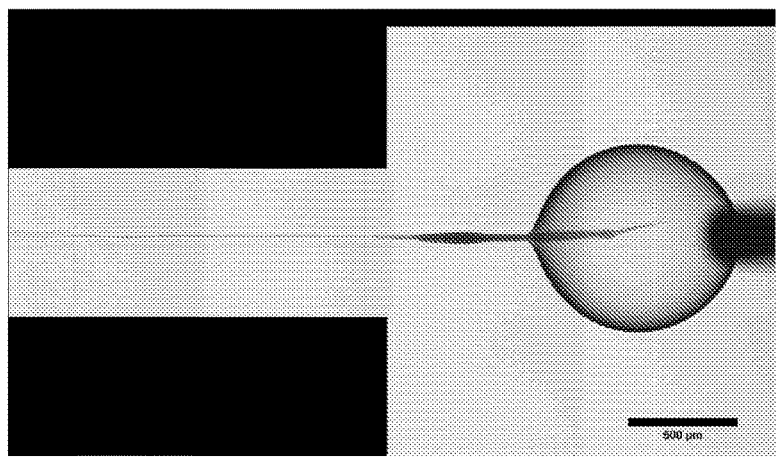
Figure 19:
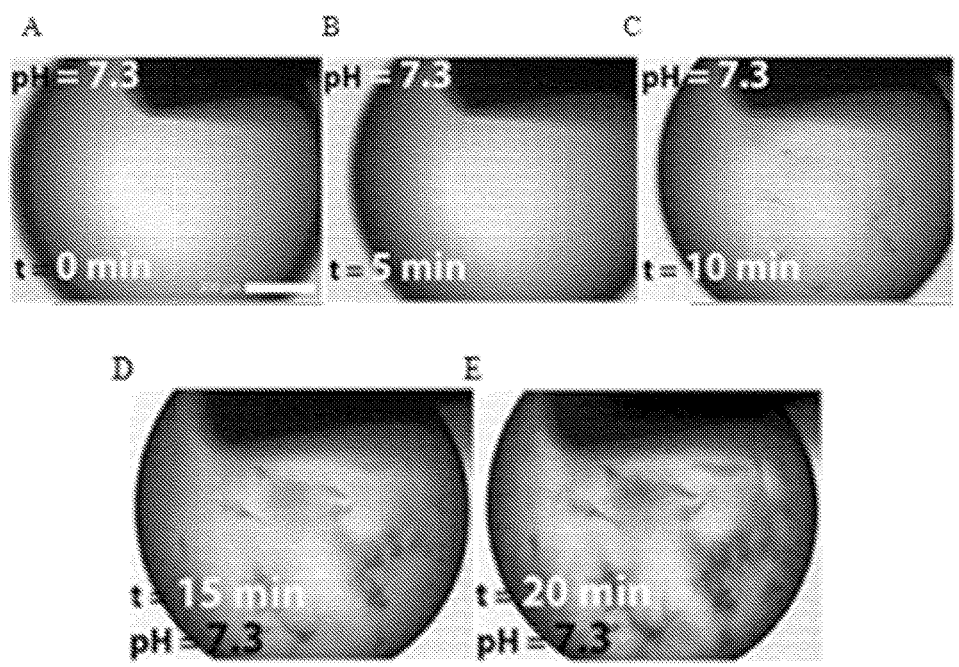
FIG. 19A-E are representations of time series images of collagen polymerization under silicone oil, where a long wait time caused the collagen solution to polymerize, and the drawn fibrils were not highly-organized.

A feature of the assembly method described herein is that the prefibrillar solution does not require, and in fact should not contain, fibrils or fibers in the prefibrillar solution. Fibril or fiber assembly in the solution prior to application of extensional forces has been associated with a decrease in fibril alignment in the final product. FIG. 19A-E are representations of time series images of collagen polymerization under silicone oil to prevent any changes in ionic strength or pH. Specifically, the images are of microvolumes of 3.0 mg/ml collagen that assembled under silicone oil at 25° C. In the images, the scale bar is 200 μm. The images show the progression of the polymerization as a function of time (at 0 minutes, 5 minutes, 10 minutes, 15 minutes, 20 minutes at pH=7.3). In addition to providing assembly kinetics, these images also detect differences in collagen morphology. FIG. 19E show that the solution possesses distinctly smaller, shorter fibrillar domains. These images show that if a fiber was pulled from a solution that was already polymerized (as is the case at 20 minutes), the fibrils would be short, highly entangled, and greatly disorganized. Similarly, FIGS. 17A-B are representations of DIC images showing highly entangled, greatly disorganized fibers that were not generated using the disclosed methods. These images show fibrils that were drawn after the collagen solution had polymerized and reached steady-state. As shown in FIGS. 17A-B, the resulting fibrils were highly-entangled and not organized. The concentration of the solutions used were 1.2 mg/ml.

In some aspects, this disclosure addresses methods and devices to generate an organized array of collagen fibrils from the bottom-up. In some aspects, these arrays are biological and mechanically functional upon implantation. Previous efforts to produce natural collagen-based tissues from the bottom-up were hampered by a substantial gap in our knowledge of how tissue is formed. Most importantly, our understanding of the assembly kinetics from the moment collagen monomers exit the cell to the time when organized tissue has been created is limited. (Cowin 2000; Cowin 2004). Progressing to the generation of highly-aligned fibrils within a larger fiber or lamella has been slow and suffered from numerous shortcomings. None of the methods known in the prior art have produced structures with native tissue organization and precise alignment control.

Although not bound by any theory, the disclosure is based on the theory that the cell indirectly influences the formation and growth of collagen fibrils locally, but that ultimate organization and long-range alignment arise because collagen fibril assembly depends on force/strain. The disclosed methods and devices allow control of extensional and shear strain and produce highly-organized arrays of collagen and/or elastin fibrils and fibers.

The disclosure, in some respects, is based on the discovery that collagen's mechanosensitivity can be used to produce multi-scale, hierarchical structures that strongly mimic native tissues (including but not limited to blood vessels to bones), and that the extensional strain used to generate such structures can be controlled. In some aspects, the disclosure includes methods and devices for using microfluidic devices to generate collagen fibers/lamellae with precisely-controlled internal fibril alignment. The disclosed methods and devices use extensional strain with low shear rate to generate a highly organized array of collagen fibrils. The concentration of prefibrillar collagen solution, pH, and ionic strength are adjusted or set to induce fibril formation.

The disclosure is informed by our "smart matrix" model in which we suggested that collagen is stabilized/retained and assembles when subjected to applied tensile strain. The disclosed methods and devices allow precise control of collagen fibril organization at the nanoscale and allow bottom-up construction of highly-mimetic tissue surrogates. The disclosure allows engineering-level process control over collagen assembly.

Collagen

In some embodiments, the disclosed methods and devices generate a highly organized array of collagen fibrils. Collagen is the most abundant protein in the extracellular matrix (ECM) of vertebrates and is the most common structural molecule in tensile load-bearing applications. More than 29 different collagenous sequences are known. Fibrillar collagens (e.g., Types I, II, III, V and XI) are the principal structural component in load-bearing extracellular matrix, which provides a network for cells to interact and form three dimensional, multi-cellular organisms. Collagen possesses a linear-helical structure including three left-handed helical alpha chains whose complementary amino acid sequence results in the formation of a right-handed supramolecular triple helix. Collagen contains the repetitive sequence amino acid sequence Gly-X-Y, where X is usually proline, and Y is usually hydroxyproline.

Various types of collagen can be used in the methods and devices described herein and can be isolated or derived from a natural source, manufactured biochemically or synthetically, produced through genetic engineering, or produced through any other means or combinations thereof. In addition, collagen is commercially available (e.g., from Inamed Biomaterials, Fremont, Calif.; and FibroGen, Inc., San Francisco, Calif.). Natural sources include, but are not limited to, collagens produced by or contained within the tissue of living organisms (including but not limited to cows, pigs, birds, fish, rabbits, sheep, mice, rats, and humans). Natural collagen can be obtained from, for example, tendons, bones, cartilage, skin, or any other organ by any known extraction method. Exemplary sources include rat tail tendon and calf skin.

Some collagens useful in the methods and devices described herein include, but are not limited to, collagen Types I, II, III, IV, V, VI, VII, VIII, IX, X, XI, XII, XIII, XIV, XV, XVI, XVII, XVIII, and XIX. Synthetic collagen can include collagen produced by any artificial means, and numerous methods for producing collagens and other proteins known in the art can be used. For example, synthetic collagen can be prepared using specific sequences, such as specific amino acids that are the same or that differ from natural collagen. Engineered collagen can be produced by any method known in the art including, for example, polypeptide synthesis.

Figure 16:
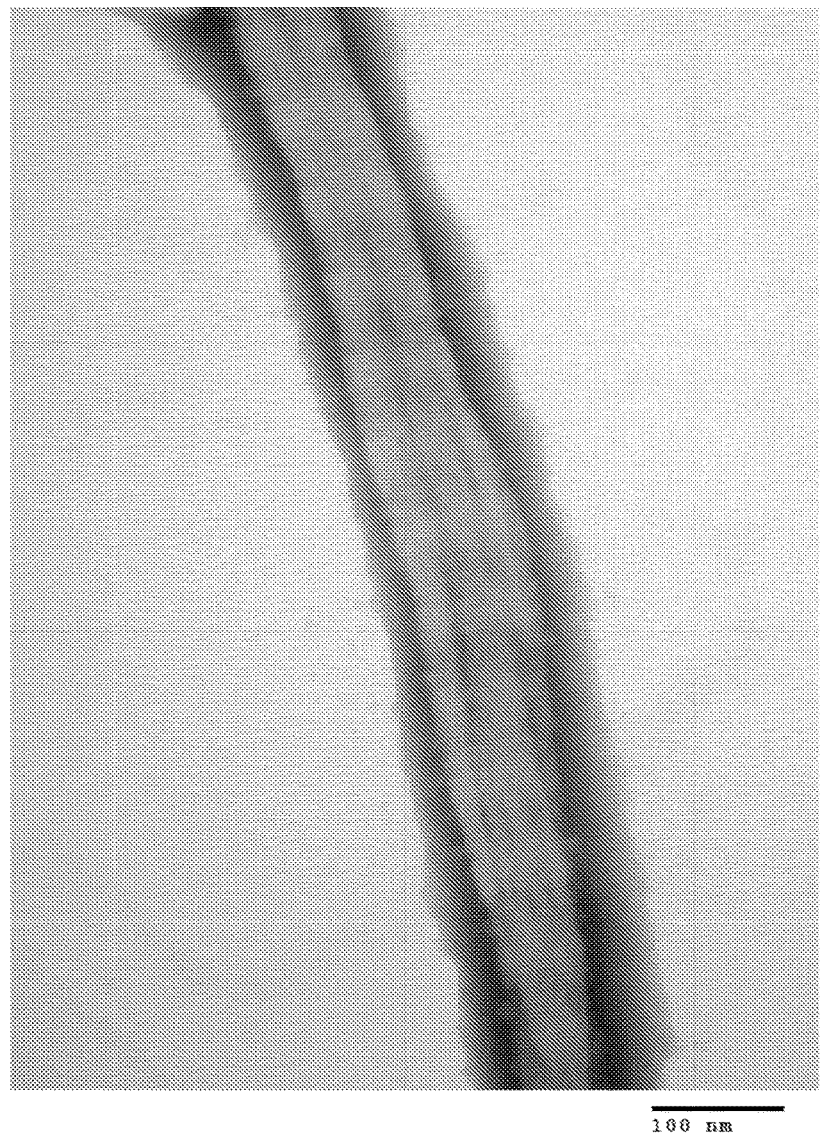
FIG. 16 is a representation of a TEM image of an isolated fibril showing D-banding produced from embodiments of the disclosed methods.

In some embodiments, the organized array of fibrils comprise D-banded collagen fibrils. FIG. 16 is a representation of a TEM image of an isolated fibril showing D-banding produced from embodiments of the disclosed methods. FIG. 16 shows collagen banding in the fibril of a fiber produced from elongational strain, and the D-banding is mimetic of natural collagen tissue. The fibril was generated from a droplet of neutralized collagen solution at 6 mg/ml, which was drawn at a rate of 275 μm/sec. After this, the fibril was incubated at 37° C. in a PBS containing 50 μg/ml of the proteoglycan decorin for 48 hours. The fibril was then placed in a tissue grinder, and fibrils were collected on a TEM grid for imaging.

Fibrous Proteins

In some embodiments, the disclosed methods and devices generate a highly organized array of other types fibrils, including but not limited to elastin fibrils. Elastin is a fibrous protein that can impart flexibility to a structure. Elastin is found naturally in certain tissues as part of the extracellular matrix. The disclosure can be used to generate a highly organized array of other fibrous proteins and proteins that impart flexibility, including but not limited to elastin, collagen, and fibronectin, or combinations thereof. Any non-naturally occurring protein that mimics the properties of such proteins are also contemplated.

Structural Arrangement of Collagen in Native Load-Bearing ECMs

The mechanics of native collagenous matrices are based on the nanoscale organization of the collagen fibrils. With the exception of bone (due to its unique remodeling mechanism including osteon or haversion systems), the structure of load-bearing tissues is "set" during development and does not appreciably change in the general long-range organization in the adult. There are principally two organizational regimes for collagen fibrils: 1) uniaxial prismatic cylinders, and 2) uniaxial sheets or "lamellae." In the case of uniaxial sheets or lamella, three-dimensional structures are "built-up" by successive layering of these lamellae in stacks where the angle between lamellae is changed. The stacks can be formed in concentric cylinders (such as in lamellar and osteonal bone, annulus fibrosus) or nested hemispheres (such as in cornea). These structures are actually two-dimensional (plus) and are naturally optimized for bearing tension in the plane of the lamellae (such as in cornea) or for resisting torsion (such as in annulus fibrosus).

Prefibrillar Solution

The methods and devices described herein involve collagen and/or elastin solutions, such that the collagen and/or elastin are prefibrils that have not aggregated into fibrils or fibers. Although collagen is used as an example of a prefibrillar solution, the disclosed methods and systems are not limited to collagen and may include other fibrous proteins or related synthetic materials discussed herein.

The methods and devices described herein involve prefibrillar solutions, which include predominantly collagen monomer solutions, with additional molecules, e.g., collagen modulating molecules such as extracellular matrix molecules. Such molecules include, but are not limited to, proteoglycans (such as perlecan, versican, syndecan, decorin, lumican, fibromodulin, aggrecan, and biglycan), proteoglycan core proteins, glycosaminoglycans (such as hyaluronic acid, chondroitin-4 sulfate, chondroitin-6 sulfate, dermatan sulfate, heparin, heparin sulfate, and keratin sulfate), fibril forming collagens, FACIT collagens, enzymes (such as matrix metalloproteinase or lysyl oxidase), fibronectin, and/or elastin. In some embodiments, the concentration of the prefibrillar solution is about 1.2 mg/ml to about 500 mg/ml; about 2.0 mg/ml to about 300 mg/ml; about 2.4 mg/ml to about 100 mg/ml.

In some embodiments, the prefibrillar solution includes cells, including stem cells or fibroblasts. The cells can be incorporated into the prefibrillar solution before, during, or after the application of extensional strain.

In some embodiments, the solution comprises a co-nonsolvency agent, which is an agent that is not miscible or only mixes slightly with the fibrillar solution. In some embodiments, these agents are molecules (for example, hypertonic agents) that compete with collagen and/or elastin for available water and thus concentrate the collagen and/or elastin solution. Such hypertonic agents include but are not limited to polyethylene glycol (PEG), hyaluronic acid (HA), a proteoglycan, glycosaminoglycans (GAGs), or a combination thereof. These agents can be added to a solution containing collagen prefibrils prior to or after polymerizations described herein. Surprisingly, in some aspects, the disclosed methods use extensional strain with low shear rate to induce prefibrillar collagen and/or elastin solutions to assemble into an organized array of collagen fibrils. In some embodiments, this extensional strain is applied to prefibrillar solutions with prefibrils that have not self-assembled into fibrils, including collagen and/or elastin fibrils. The disclosed methods and devices generate highly-organized fibrils in a discontinuous dispersion in a solution rather than an already-assembled array of fibrils.

In some instances, collagen is polymerized as described herein, and the collagen organization is further refined by subjecting the initial collagenous construct to cross-linking, mechanical strain, and/or enzymes to cull unwanted (unstrained) fibrils (see, e.g., Ruberti et al., *Biochem. Biophys. Res. Commun.* 336:483-489 (2005)). Collagen fibrils are cross-linked to facilitate mechanical strain. Any suitable crosslinking agent known in the art can be used, including, without limitation, formaldehyde, lysyl oxidase, hexamethylene diisocyanate, glutaraldehyde, polyepoxy compounds, gamma irradiation, and ultraviolet irradiation with riboflavin. The crosslinking can be performed by any known method (see, e.g., Bailey et al., Radiat. Res. 22:606-621 (1964); Housley et al., Biochem. Biophys. Res. Commun. 67:824-830 (1975); Siegel, Proc. Natl. Acad. Sci. U.S.A. 71:4826-4830 (1974); Mechanic et al., Biochem. Biophys. Res. Commun. 45:644-653 (1971); Mechanic et al., Biochem. Biophys. Res. Commun. 41:1597-1604 (1970); and Shoshan et al., Biochim. Biophys. Acta 154:261-263 (1968)).

The methods described herein can be used to "sculpt" collagenous ECMs through application of extensional elongation and also exposure to collagen-degrading enzymes including, without limitation, collagenase (e.g., bacterial collagenase), cathepsin, and matrix metalloproteases (MMPs). Thus, in some instances, collagen is contacted with a collagen-degrading enzyme and simultaneously subjected to extensional elongation.

Applications

Applications of the disclosed methods include making organized collagen scaffolding and tissues for repair; providing an alignment guide for other molecules (for example, nanotubes, such as carbon nanotubes); and for connective tissue regeneration in the laboratory. The methods represent a new approach for acellularly engineering the extracellular matrix.

Collagen produced by the methods and devices described herein can be used to engineer tissues or organs including, but not limited to, bone, dental structures, joints, cartilage, skeletal muscle, smooth muscle, cardiac muscle, tendons, menisci, ligaments, blood vessels, stents, heart valves, corneas, ear drums, nerve guides, tissue or organ patches or sealants, a filler for missing tissues, sheets for cosmetic repairs, skin (sheets with cells added to make a skin equivalent), soft tissue structures of the throat (such as trachea, epiglottis, and vocal cords), other cartilaginous structures (such as articular cartilage, nasal cartilage, tarsal plates, tracheal rings, thyroid cartilage, and arytenoid cartilage), connective tissue, vascular grafts and components thereof, and sheets for topical applications or for repair or replacement of organs (such as livers, kidneys, and pancreas).

In some situations, the collagen is produced having a predetermined shape, such as a predetermined shape dictated by external and internal templates described herein. In specific instances, the templates can be shaped, for example, in the shape of a nerve guide, skin or muscle patch, fascial sheath, vertebral disc, knee meniscus, ligament, tendon, or a vascular graft for subsequent use in vivo. The collagen can also be shaped to fit a defect or site to be filled, e.g., a site where a tumor has been removed or an injury site in the skin (e.g., a cut, a biopsy site, a hole or other defect) or to reconstruct or replace a missing or shattered piece of bone. The methods described herein allow for great flexibility and the ability to customize the collagen to various shapes. Specific geometries include, but are not limited to, a cylindrical shape, a flattened oval shape, capillary tubes (as in tendon), and concentric cylinders (as in artery, annulus fibrosus, lamellar bone).

In some instances, further shaping can be achieved by manually processing the formed collagen. For example, formed collagen can be sutured, sealed, stapled, or otherwise attached to one another to form a desired shape. For example, the method can be used as a printer head, e.g., that the desired shape can be directly printed in a three-dimensional printer.

Microfluidic Devices and Methods

In some aspects, fibrils can be obtained in a continuous process or on a larger scale using microfluidic processes and devices. The disclosure includes microfluidics devices that include a microfluidic structure; a channel on or within the structure comprising at least one inlet and at least one outlet; where a first microfluidic inlet on the structure is configured to transport a solution comprising collagen and/or elastin at a controlled flow rate, such that the collagen and/or elastin are prefibrils that have not assembled into fibrils. In these devices, each of the plurality of inlets configured to merge into the channel that connects to the at least one outlet, such that the controlled flow rate produces an extensional and strain that are sufficient to induce the prefibrils to assemble into an organized array of fibrils. In some embodiments, the extensional strain is generated by a pressure difference between the inlets and the outlet. In other embodiments, as described herein, a drawing probe is used to apply the extensional strain. In some embodiments, the microfluidic structure is a flat structure or a cylindrical structure.

In some embodiments, the device includes a second microfluidic inlet on or within the structure that is configured to transport a biocompatible, immiscible fluid. In some embodiments, the fluid is silicone oil or perfluorodecalin. In some embodiments, the fluid has low shear viscosity. In some embodiments, this fluid is a low viscosity, lubricating layer that can dissipate the shear effects near the wall of the microfluidics device. In other embodiments, we can tune the viscosity of this layer to control the level of shear strain during polymerization. Thus, the resulting array of fibrils can have different mechanical properties, for example, some are more flexible fibrils, as opposed to other fibrils that are less flexible.

In some embodiments, the device includes a third microfluidic inlet on the structure that is configured to transport a fluid that neutralizes and concentrates the collagen solution. In some embodiments, this fluid allows for the exchange of ions and water molecules to adjust the pH, ionic strength, and concentration of the solution. In some embodiments, the fluid that neutralizes and concentrates the collagen solution includes polyethylene glycol, hyaluronic acid, or glycosaminoglycans. In some aspects, the disclosed devices and methods are configured to control the extensional strain-rate, pH, ionic strength, and/or concentration of the collagen solution. In some embodiments, the concentration of the prefibrillar collagen solution is about 1.2 mg/ml to about 500 mg/ml; about 2.0 mg/ml to about 300 mg/ml; about 2.4 mg/ml to about 100 mg/ml.

In some aspects, methods are disclosed for using the microfluidics devices described herein. The methods include providing a prefibrillar solution to the first microfluidic inlet channel; and applying a controlled extensional strain in a direction away from the flow of the solutions, thereby inducing the prefibrillar solution to polymerize and to assemble into an organized array of collagen and/or elastin fibrils. In some embodiments, the methods include capturing the organized array of collagen fibrils using an instrument that draws the fibers at a rate equal to or faster than the flow rate of the solutions. In some embodiments, the instrument is a spool.

In some aspects, the disclosed devices and methods allows control of extensional strain in the method of forming an organized array of collagen fibrils. In mammalian tissues, thousands of cells secrete collagen in confined, mechanically-loaded spaces to generate load-bearing tissue.

Figure 6:
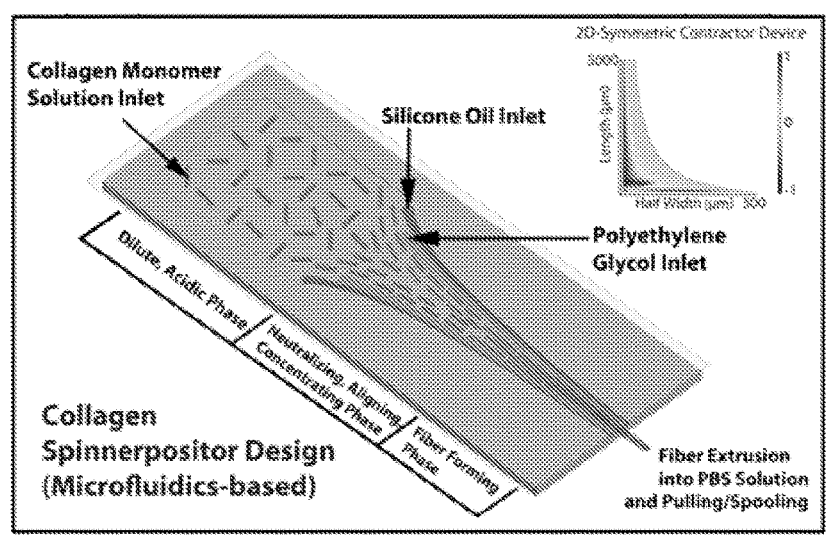
FIG. 6 is a schematic illustration of certain embodiments of the disclosed methods and microfluidics devices.

As discussed in more detail herein, FIG. 6 depicts embodiments of methods and devices to produce collagen fibrils with highly-controllable collagen fibril organization. In the three-solution co-flow hyperbolic device, the extensional strain-rate, pH, ionic strength and concentration of the collagen solution are controlled.

Figure 13:
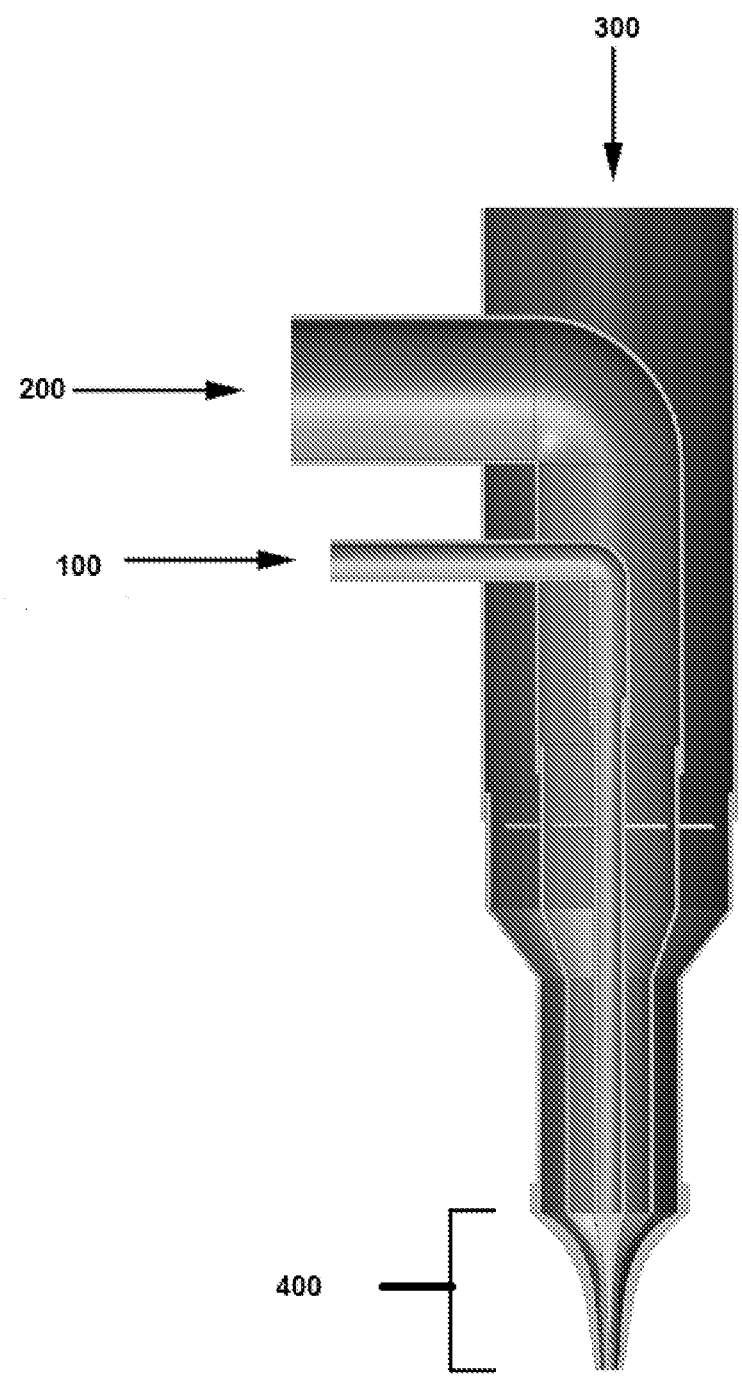
FIG. 13 is a schematic representation of cylindrical microfluidic devices according to some embodiments.

In some aspects, the disclosed devices apply an elongational flow to a prefibrillar solution. The pH, ionic strength, and concentration of the prefibrillar solution are adjustable. FIG. 13 is a schematic representation of the disclosed embodiment. The figure shows a cross-sectional view of a cylindrical microfluidic device that has a nozzle to produce extensional strain. Inlet 100 is the inlet for the central flow of the prefibrillar solution. Inlet 200 is the inlet for a hypertonic solution that can help concentrate the prefibrillar solution, and allows for exchange of fluids, ions, and other small molecules. Inlet 300 is the inlet that allows for co-flow of a lubricating solution to reduce the shear stress. In some embodiments, the precursor solution 100 may also contain enzymes, other extracellular proteins, cells, or synthetic structural reinforcements (e.g. carbon nano tubes). The material collected at the outlet of the device may experience a collection at a rate equal to or faster than the extrusion rate to further induce extensional strain. The nozzle 400 allows hyperbolic contraction for extensional flow and is where polymerization is triggered.

Figure 14:
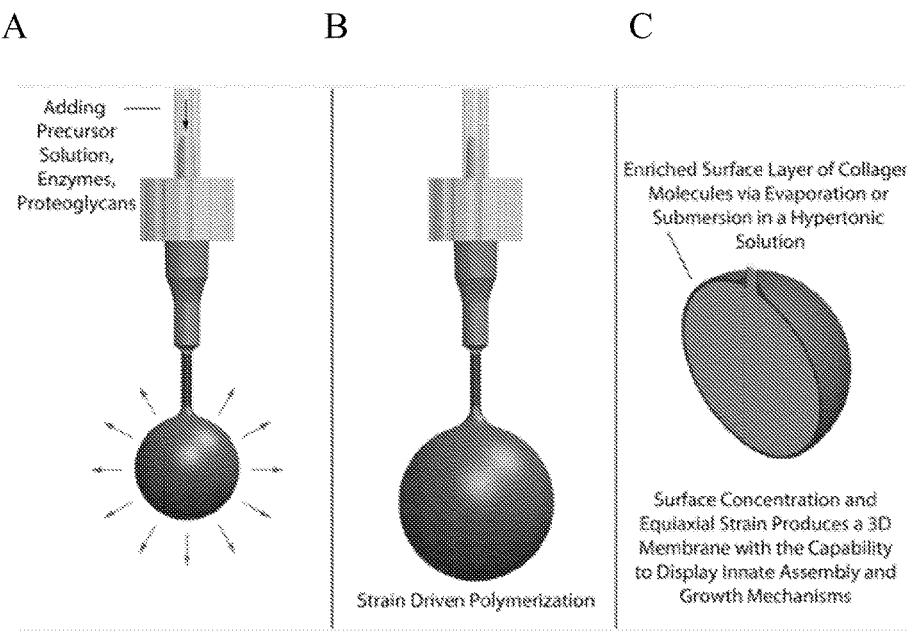
FIGS. 14A-C are schematic representations of microfluidic devices according to some embodiments.

In some aspects, the disclosed devices apply a two-dimensional surface strain to a prefibrillar solution. FIG. 14 is a schematic diagram of an embodiment that applies two-dimensional surface strain to a prefibrillar solution. The surrounding environment produces an enhanced surface concentration of the prefibrillar solution on the sphere. This enhanced surface concentration may be achieved in multiple ways, e.g. through evaporation at a rate exceeding the molecular diffusion away from the surface or through an interaction with a hypertonic solution. Conversely, a prefibrillar solution with a high starting concentration may be used. The sphere then receives an addition of fluid, which may contain fresh prefibrils, enzymes, cells, and/or proteoglycans. This equiaxial strain at the surface of the sphere, with the enriched prefibrils concentration, can generate aligned polymerization in the direction of the extensional strain and provide an assay for extracellular matrix growth and remodeling. The disclosed method can be used in the presence of a neutrally buoyant solution to minimize spherical distortion from gravitational effects.

Figure 15:
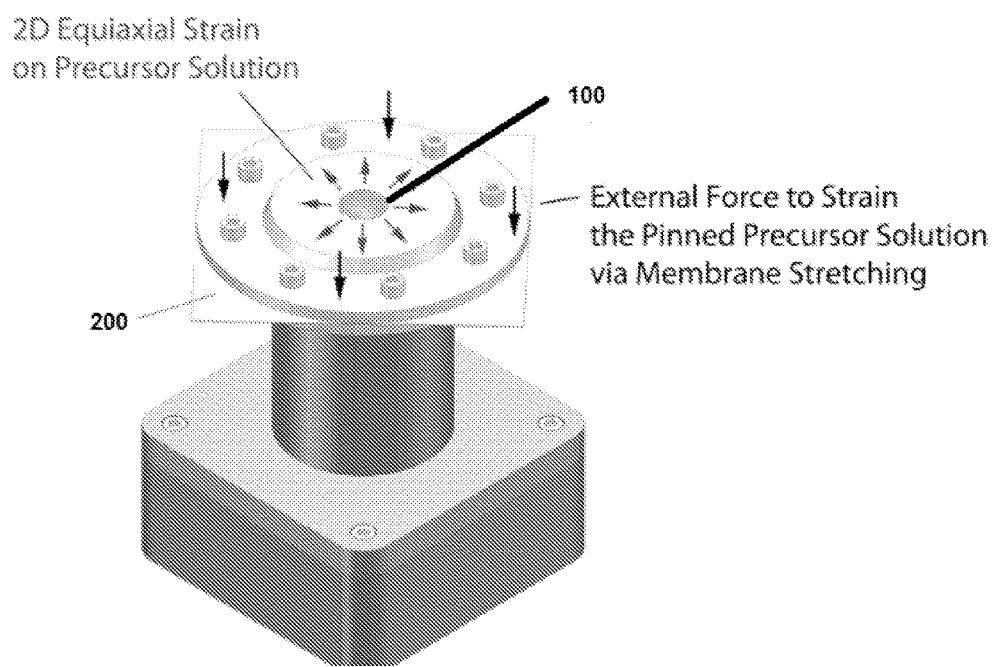
FIG. 15 is a schematic representation of microfluidic devices according to some embodiments.

In some aspects, the disclosed devices apply a two-dimensional equiaxial strain to a prefibrillar solution. FIG. 15 is a schematic diagram of an embodiment that applies two-dimensional equiaxial extensional strain to a prefibrillar solution. In this Figure, the device has an elastic membrane 200 with a center hole cutout, which will expand equiaxially as the membrane is stretched. The prefibrillar solution 100 is geometrically pinned in the center hole cutout by fluid adhesion. The surrounding environment produces an enhanced surface concentration for the droplet/layer of fluid. This may be achieved in multiple ways, e.g., through evaporation at a rate exceeding the molecular diffusion away from the surface or through an interaction with a hypertonic solution. Conversely, a solution with a high concentration of prefibrillar solution can be used. The equiaxial strain at the periphery of the fluid generates aligned fibrillar polymerization in the direction of the strain field and provides an investigatory assay for extracellular matrix growth and remodeling. In some embodiments, additional prefibrillar solution, enzymes, cells, proteoglycans, can be added before, during, or after strain is applied.

The invention is further illustrated by the following examples. The examples are provided for illustrative purposes only. They are not to be construed as limiting the scope or content of the invention in any way.

EXAMPLES

The invention is further illustrated by the following examples, provided for illustrative purposes only. They are not to be construed as limiting the scope or content of the invention in any way.

Example 1

Collagen Droplets

In some aspects, the methods used collagen prefibrils (for example, fibril forming types I, II, III, V and XI) that accumulate at an interface or in bulk solution. The concentration of the accumulated monomers is in the range of about 1.2 mg/ml to about 500 mg/ml. In some embodiments, the range is about 2.0 mg/ml to about 300 mg/ml. In some embodiments, the range is about 2.4 mg/ml to about 100 mg/ml. After the collagen prefibrils has accumulated or concentrated, a drawing probe or array of drawing probes was made to contact the solution interface or bulk solution. Surprisingly, an organized collagen fibril or series of fibrils were drawn from the solution. In some embodiments, the drawing rates are in the range of about 0.01 micrometer/second to about 1 meter/second. In other embodiments, the drawing rates are in the range of about 1 micrometer/second to about 1 cm/second. During the drawing of the fibril, the temperature, ionic strength, pH and buffers in the solution all are adjustable parameters.

In further embodiments, the fibrils may be drawn through any distinct interface where the collagen solution meets a second fluid. If the second fluid is a gas, then the humidity of the gas is controlled in the range from 0%-100% relative humidity (RH). In some embodiments, the RH has a range of from 0%-50%; 0%-40%; 0%-30%, 0%-25%; and 0%-20%; 0%-15%; and 0-10%. In some embodiments, the RH is 10%.

In some embodiments, after a fibril or arrays of fibrils is drawn, they may be further exposed to a solution that promotes re-crystallization. In some embodiments, this solution is any collagen fibril forming buffer, which may include but are not limited to hypertonic agents such as polyethylene glycol (PEG), hyaluronic acid (HA), or glycosaminoglycans (GAGs). In some embodiments, the methods include applying tension to the organized array of collagen fibrils as the fibrils recrystallize.

In some embodiments, the disclosed methods include one or more post-processing steps to further refine the collagen fibrils, such as exposure to more collagen monomers, collagenolytic enzymes, and proteoglycans. In some embodiments, tension may be applied to the fibril or arrays of fibrils while they are recrystallizing.

It is contemplated that collagen concentration ranges, the magnitude and distribution of strain, and the rehydration environment in the methods can be changed.

Figure 3:
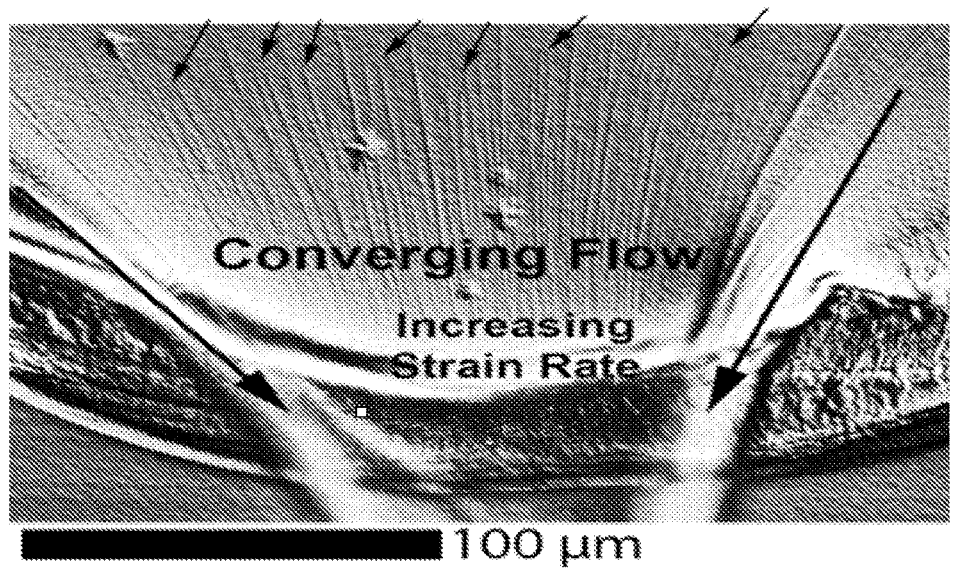
FIGS. 3A-B are representations of DIC images showing the necking region of a collagen fiber pulled from a droplet of prefibrillar collagen solution using embodiments of the disclosed methods.
Figure 3:
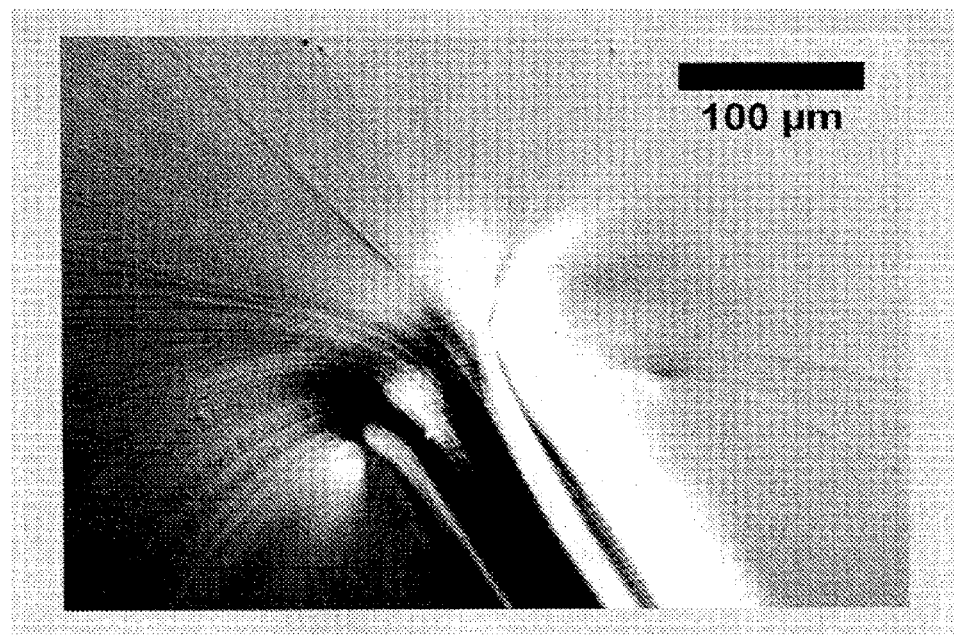

Surprisingly, the disclosed methods produce organized fibrils at low draw speeds from droplets. Extensional flow is where fluid velocity in the direction of the longitudinal axis increases as the fluid flows. In this type of extensional flow, the extensional profile is designed to dominate over shear effects such that the prefibrillar collagen aligns in the direction of the longitudinal axis of the disclosed devices. FIGS. 3A-B show representations of the geometry of the droplet at the necking region, which is the location where the fiber is being generated. Using COMSOL software to model the fluid dynamics, FIGS. 3A-B show that this fluid flow profile is dominated by extension where the collagen fiber exits the droplet, which leads to the high degree of alignment of the fibrils.

Figure 7:
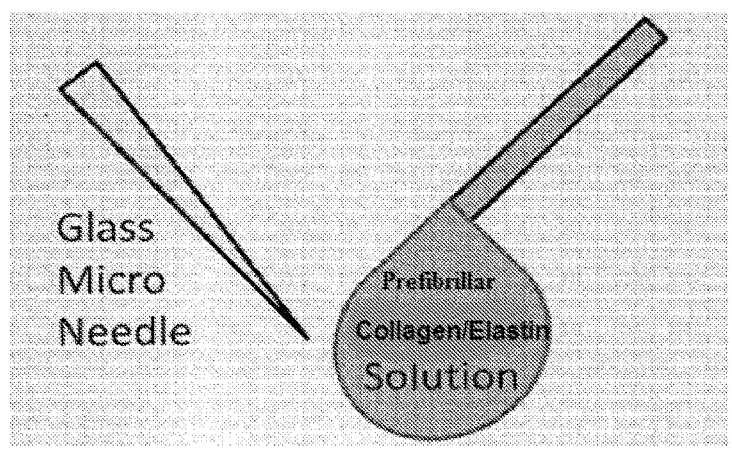
FIG. 7 is a schematic illustration of embodiments of disclosed methods and devices.

FIG. 7 is a schematic illustration of drawing a fibril using, for example, a glass micro needle, from a droplet of collagen solution. Materials. Atelo-collagen was used at a concentration of 2.4 mg/mL in PBS at a pH of 7.3 in room temperature. The droplet size was about 10 to about 20 µl. The pulling velocity was about 5 to about 100 µm/second.

FIG. 2A is a representation of a DIC image showing a collagen fibril being drawn by a glass microneedle from a droplet of collagen solution. In FIG. 2B, the drawn fibril is shown in a horizontal position. The fibril is drawn by a glass microneedle 100 from a droplet of prefibrillar collagen solution 110. FIGS. 2A-B were generated using a short 5 minute wait step. The image shows generation of a continuous fiber by using molecular crowding and mechanical stimulation in the form of extensional strain.

FIGS. 9A-F is a representation of DIC time-lapse images showing collagen fiber attachment mobility. The images in FIGS. 9A-F are taken at different time points (0 seconds, 22 seconds, 33 seconds, 56 seconds, 1:11 seconds, and 1:29 seconds, respectively). These images show that the attachment point of the fiber has mobility. The attachment point can move freely because the fibrillar structure only begins to initiate a short distance from the necking region, as shown in FIGS. 3A-B.

Figure 10:
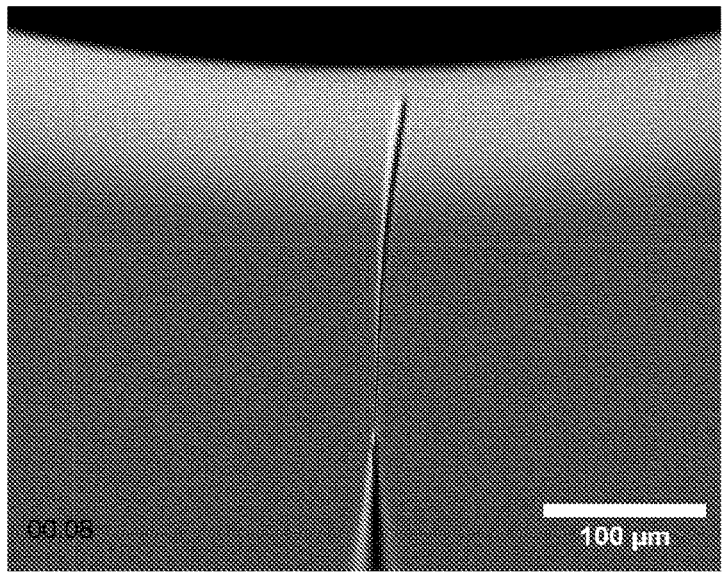
FIGS. 10A-B are representations of DIC images showing collagen fiber reattachment of a fiber generated using embodiments of the disclosed methods.
Figure 10:
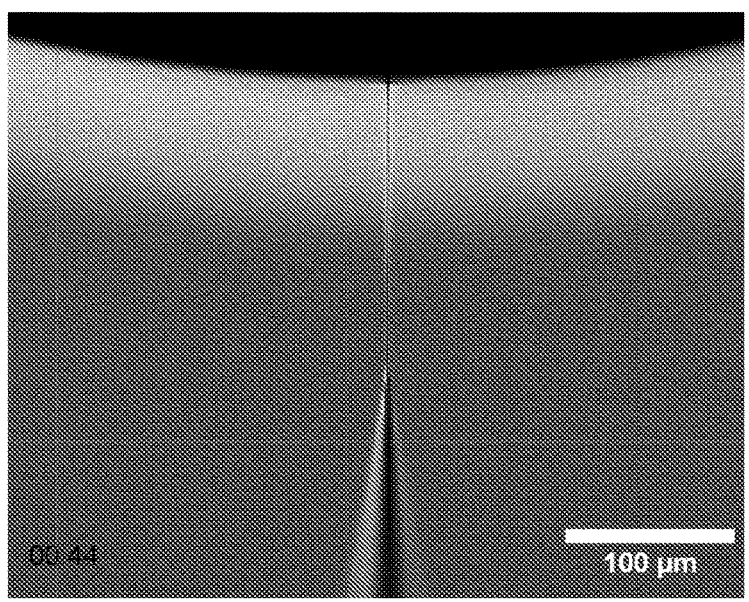

FIGS. 10A-B are representations of DIC time-lapse images showing the ability of the fiber to repair after rupture, and that continuing pulling the fibril leaves only a minor defect at the repair site. In FIG. 10A, the fiber had detached from the attachment point at 8 seconds. FIG. 10B shows fibril reattachment at 44 seconds after the fibril was continually pulled.

Figure 20:
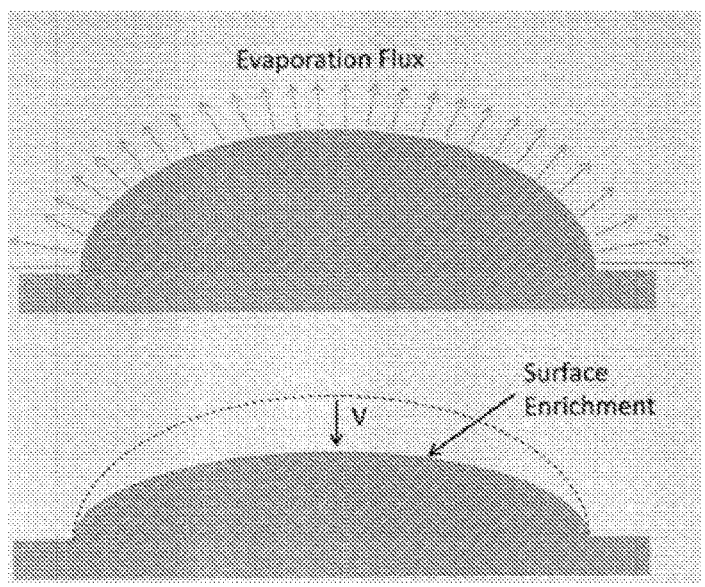
FIG. 20 is a schematic illustration to demonstrate the concept that while evaporative concentrating is driving the surface crowding, hydrophobic protein adsorption can play a similar role, although to a lesser degree.

FIGS. 12A-D is a representation of a DIC image showing collagen fiber formation under certain conditions. The fibril was pulled from a 3 mg/ml prefibrillar collagen solution when the droplet was under oil. FIG. 20 demonstrates the concept that while evaporative concentrating is driving the surface crowding, hydrophobic protein adsorption can play a similar role, although to a lesser degree. In addition, pulling a fibril under oil demonstrates that the process is not the result of evaporation-driven changes in pH or ionic strength.

Figure 11:
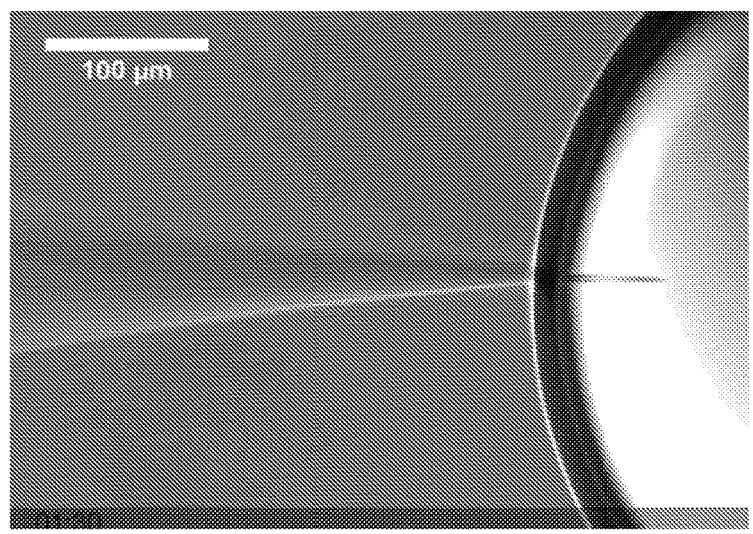
FIG. 11A-B are representations of DIC images showing collagen fiber formation according to embodiments of the disclosed methods.
Figure 11:
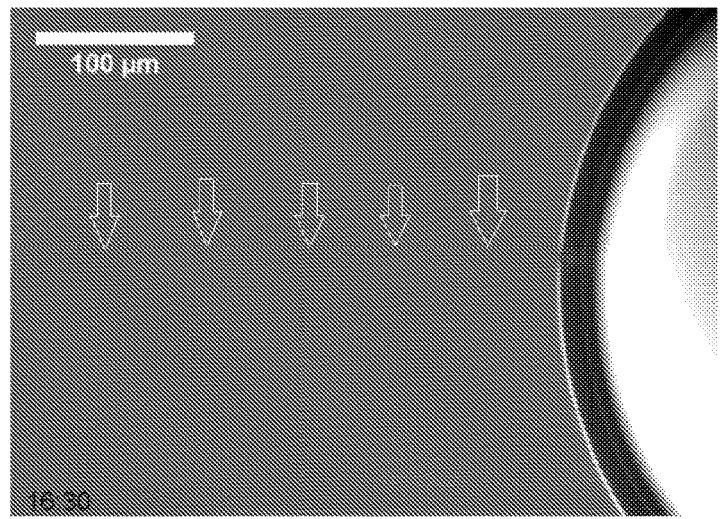

FIG. 11 is a representation of a DIC time-lapse image where extraction was performed by drawing a fibril from a droplet solution with a layer of silicone oil. The attachment point was highly mobile due to the lower surface concentration due to the weaker effect of hydrophobic protein adsorption. In FIG. 11, a longer wait time was used (about 20 minutes), with a slower pull that resulted in a shorter fibril. This Figure demonstrates that evaporation is not needed to pull a fiber because it was performed under silicone oil—simply hydrophobic interaction was enough. Thus, fiber formation cannot be forced with mechanical stimulation by pulling faster. The surface should have an appropriate concentration as well.

Figure 5:
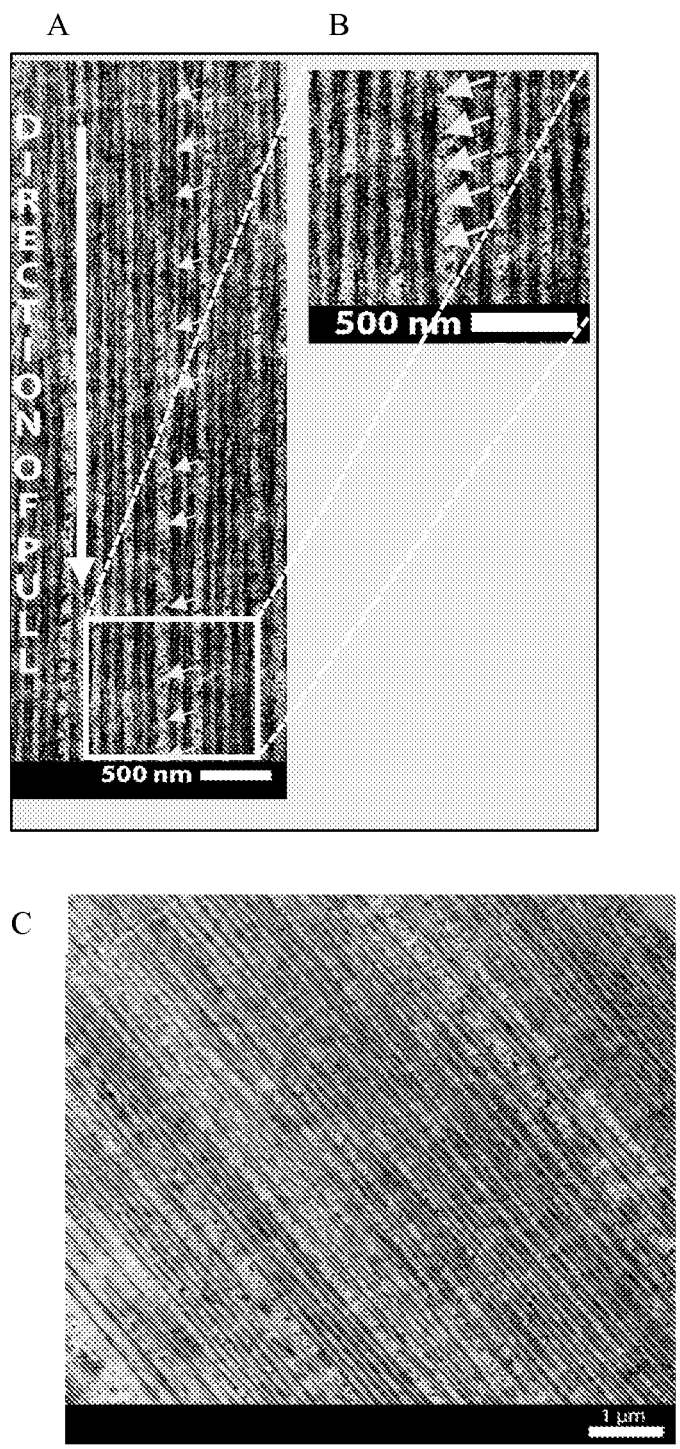
FIG. 5A-B are representations of TEM micrographs that show an organized array of collagen fibrils produced using embodiments of the disclose methods and devices.
FIG. 5C is a representation of a TEM micrograph shown at a larger scale according to some embodiments of the disclosure.

FIG. 3A-B is a representation of a DIC image that shows the necking region from the droplet where fibril formation becomes visible. Similarly, FIG. 5 is a representation of a DIC image that shows that fibril formation begins (as shown by the white arrow), and that tension triggers collagen fibril assembly.

Figure 8:
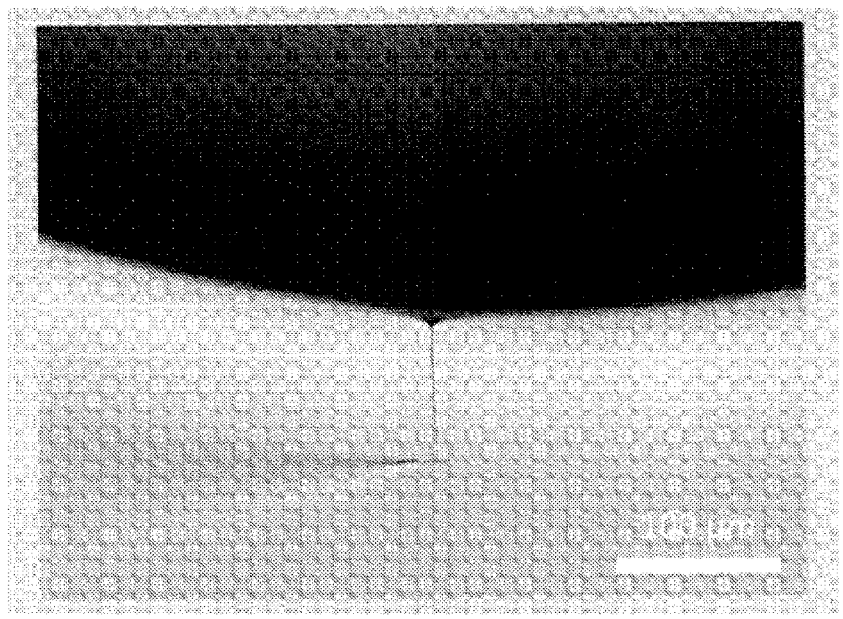
FIG. 8 is a representation of a DIC image showing a collagen fiber generated using embodiments of the disclosed methods.
Figure 9:
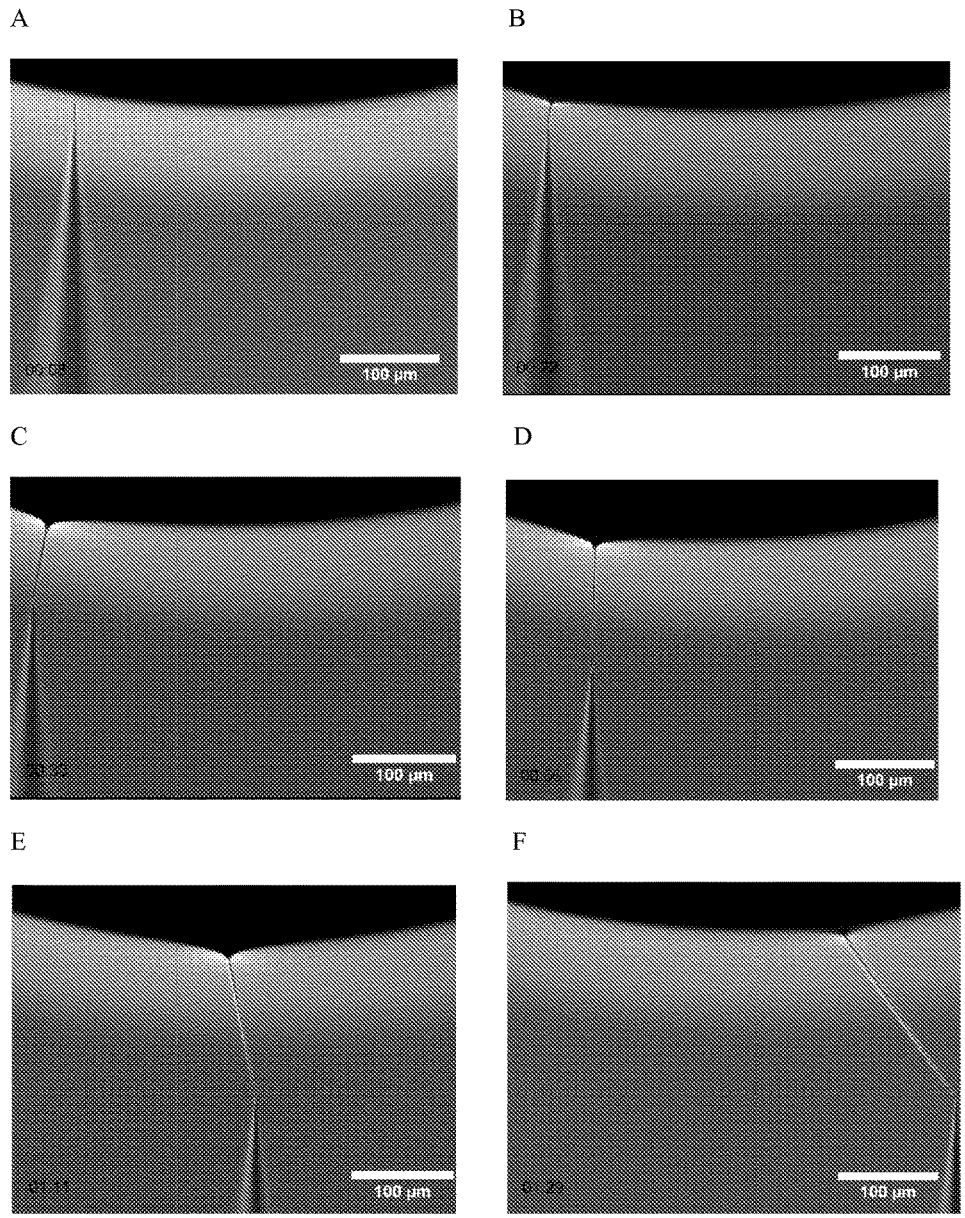
FIGS. 9A-F are representations of DIC images showing collagen fiber attachment mobility of a fiber generated using embodiments of the disclosed methods.

FIG. 2A-B is a representation showing that a thin collagen fibril was pulled directly from a droplet containing type I bovine collagen monomers according to some embodiments. In this experiment, the collagen fibril was drawn from a droplet of neutralized type I bovine collagen monomers. The concentration of the prefibrillar solution was 3.0 mg/ml at 25° C. The drawn fibril is about 10 mm×20 μm. FIG. 8 is a representation of a DIC image showing a collagen fiber being drawn by a glass microneedle from a droplet of collagen solution. In FIG. 2B, the drawn fiber is shown in a horizontal position. The fiber is drawn by a glass microneedle 100 from a droplet of prefibril collagen solution 110. FIGS. 2A-B were generated using a short 5 minute wait step. The image shows generation of a continuous fibril by using molecular crowding and mechanical stimulation in the form of extensional strain. In some aspects, the disclosure is based on the discovery that the extensional strain at the necking region where the fiber is being extracted from the droplet was an important driver of the fibrillogenesis. This figure demonstrates the continuous nature of the fibril production method, even from a small droplet of prefibrillar collagen solution.

FIGS. 3A-B are a representations of DIC images of the necking region of a droplet where the prefibrillar collagen solution dried after pulling a collagen fibril using embodiments of the disclosed methods. In FIG. 3A, the smaller arrows show the initial formation of prefibrillar collagen solution into organized collagen fibrils as they are being drawn into the neck of the droplet and strain rate increases. Similarly, FIG. 3B shows the formation of organized collagen fibrils from a different angle. In both FIGS. 3A and 3B, the fibrils are created locally—only at the necking region, and the fibrils are not observed elsewhere on the surface of the droplet. The fibrils are pulled from the solution after a short waiting period (less than about 10 minutes), which supports that the tension/extensional strain is responsible for triggering the fibrillogenesis.

Figure 4:
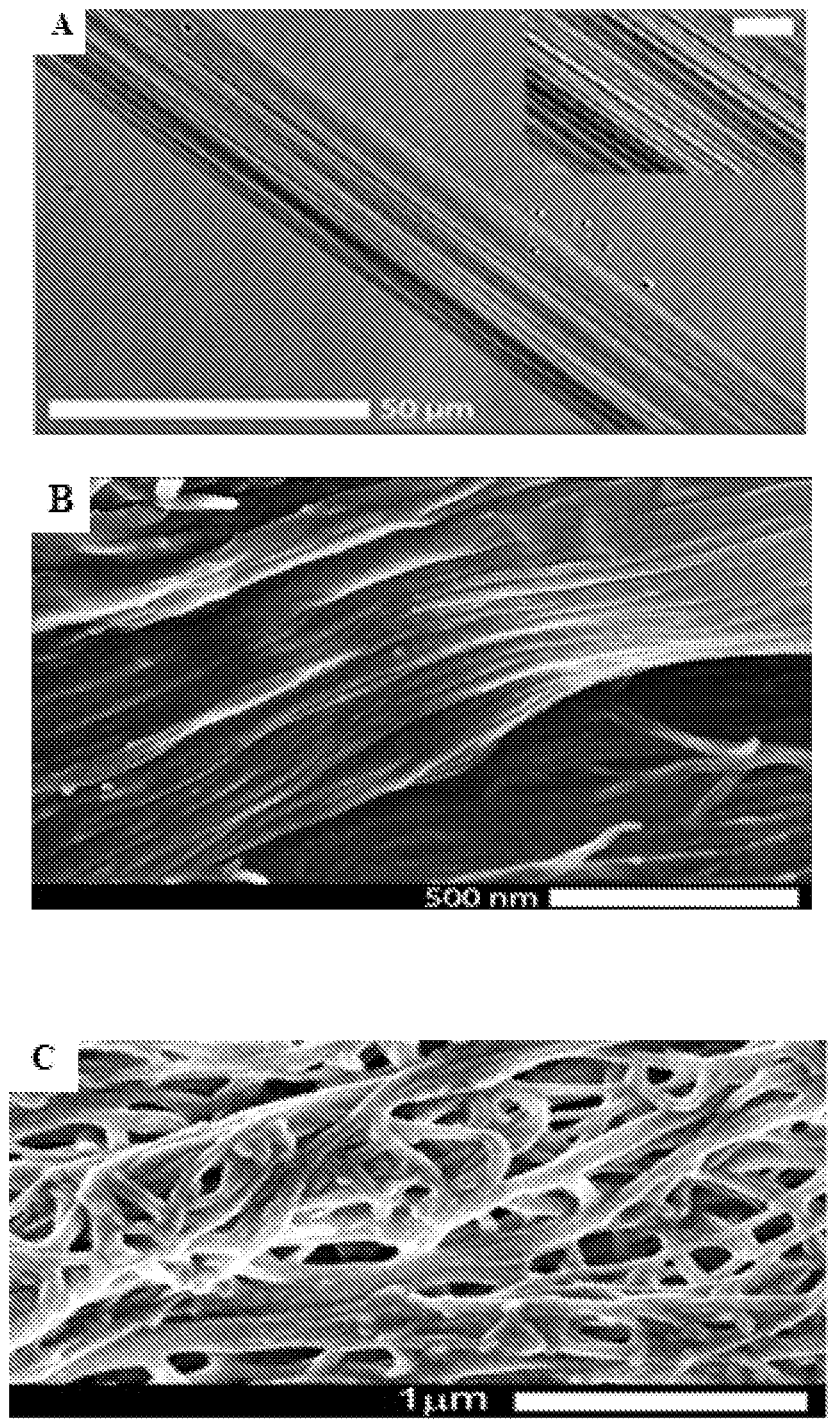
FIGS. 4A-C are representations of a DIC image (FIG. 4A) and SEM micrographs (FIGS. 4B-C) that show micro/nanoscale morphology of an organized array of collagen fibrils that were generated using embodiments of the methods and devices.

FIGS. 4A-C are representations of a DIC image (FIG. 4A) and SEM micrographs (FIG. 4B-C) that show micro/nanoscale morphology of fibrils. In FIG. 4A, the DIC image shows a surprising alignment of the organized array of fibrils generated from extensional flow (here, in one embodiment, extraction from droplets). The Figure shows the fibrillar structure, using a 20× objective, after being placed on a glass coverslip and rehydrate with phosphate buffered saline. The inset bar is 5 μm. FIG. 4A shows collagen fibrils with no evidence of internal structure in any direction other than along the fibril axis. FIG. 4B is a representation of a SEM micrograph that shows the nanoscale arrangements of highly-aligned fibrils drawn from a prefibrillar collagen solution. This shows an internal section of the fibril, generated by placing a cut into the fibril with a surgical scalpel. FIGS. 4 A-B are shown in stark contrast to FIG. 4C, which shows a disorganized collagen fibril structure produced by a fibril-forming buffer without applied extensional strain. (See Paten et al., Biomaterials, 2013. 34(11): p. 2577-87).

FIG. 5A is a representation of a TEM micrograph that shows an organized array of collagen fibrils. The small arrows show the surprising vertical alignment of fibrils of consistent diameter. The large white arrow denotes the direction of pull. FIG. 5B shows a higher magnification of the organized array of collagen fibrils. The smaller arrows follow a single collagen fibril. FIGS. 5A-B confirm the alignment shown in the SEM micrographs (FIGS. 4B-C) and again show the surprising fibril diameter regularity. Similarly, FIG. 5C is a representation of a TEM micrograph that shows an organized arrays of collagen fibrils on a larger scale.

Example 2

Microfluidic Devices and Methods

FIG. 1 is a representation of a microfluidic device according to some embodiments of the disclosure. FIG. 1A is a microfluidic, hyperbolic flow chamber. The modeled flow profile in FIG. 1B demonstrates the use of extensional flow to produce an organized array of highly aligned fibrils.

FIG. 6 depicts embodiments of methods and devices to produce collagen fibrils with highly-controllable collagen fibril organization. In the three-solution co-flow hyperbolic device, the extensional strain-rate, pH, ionic strength and concentration of the collagen solution are controlled. In some embodiments, the device takes advantage of low Reynolds number microfluidics flows to permit lateral exchange of material without the generation of overt mixing. The core flow is the prefibrillar solution, which will undergo controllable extensional strain while exchanging both ions and solvent with the second conditioning layer, Polyethylene Glycol (PEG). PEG is biocompatible and is used as an osmicant in collagen fibril forming buffers. The PEG layer concentrates the collagen and neutralizes it in the contractor such that the collagen will undergo fibrillogenesis just as it is drawn from the exit of the device (and not before). The third layer of the co-flow is a biocompatible, immiscible fluid of low shear viscosity (silicon oil or perfluorodecalin are our current first choices). This fluid plays the role of an interfacial lubricant which permits the nearly solid central column of collagen to slide out of the spinneret (reducing back pressure). In some embodiments, the disclosed methods and devices remove the air-interface while preserving its function of enhancing the concentration of collagen subject to the extensional flow. The disclosed methods and devices give a high degree of control over collagen fibrillogenesis.

In some embodiments, methods and systems for a microfluidic device that can adjust collagen concentration, extensional strain rate, and assembly kinetics are disclosed.

We determine the parameter values necessary to engineer a device that mirrors the environmental manipulations (concentration, pH and ionic strength) and extensional flow profile need to induce generation of an organized array of fibrils. We investigate the rheological properties of prefibril collagen solutions (core flow) and solutions of a candidate, co-flowing conditioning fluid: (for example, polyethylene glycol); and extract the kinetics of collagen assembly in the presence of the conditioning, co-flow fluid. A multiphysics model (COMSOL) incorporates the empirically acquired input parameters and predictively determines the optimum geometry, flow rate, draw rate and solution concentrations required to produce organized fibrils.

Studies are conducted related to the complex rheology and assembly kinetics of collagen as well as the rheology of PEG and its ability to influence collagen assembly kinetics.

Shear viscosity ($\mu$) and relaxation time ($\lambda$) of collagen and PEG solutions. The complex rheology of both collagen and PEG solutions are examined using a cone and plate, stress-controlled shear rheometer (TA DHR-3) in steady shear and in small amplitude oscillatory shear flow.

Method: Type I bovine telocollagen (obtained from Inamed, Calif.) are used in all experiments. Solutions of collagen are examined at five different concentrations (5 mg/m, 30 mg/m, 60 mg/m, 120 mg/m, and 240 mg/ml) and at multiple pH values (2, 4, 6, 7.3 and 8). Shear rate sweeps to 1000 Hz$^{-1}$, frequency sweeps to 20 Hz and temperature sweeps from 4° C.-37° C. are run). Pure, neutral pH PEG solutions of three molecular weights (4 k, 20 k, 100 k) and five concentrations (1%, 5%, 10%, 20% and 30%) are subjected to the same method as the collagen. Except where indicated, all experiments are performed in triplicate throughout the experimental series. All collagen solutions are used within one month of purchase and stored at 4° C. prior to use.

Result: Master curves are generated that relate the shear viscosity ($\mu$) of collagen and PEG solutions to pH, shear-rate, temperature, and concentration. This allows determination of the pressure and the potential shear profile in embodiments of the disclosed devices. The relaxation time ($\lambda$) of the collagen monomers in solution is determined. Relaxation time can be extremely important in flows, like that produced within a converging contraction where the PEG and collagen will be stretched and deformed when the extensional strain rate imposed on the fluid ($\varepsilon$) is greater than the inverse of the fluid's relaxation time. (Rothstein, J. P. and G. H. McKinley, J. Non-Newtonian Fluid Mech., 1999. 86(1-2): p. 61-88; Rothstein, J. P. and G. H. McKinley, J. Non-Newtonian Fluid Mech., 2001. 98: p. 33-63; Oliveira et al., Experiments in Fluids, 2007. 43: p. 437; Pipe, C. J. and G. H. McKinley, Mech. Res. Comm., 2009. 36: p. 110-120). This value of $\dot{\varepsilon}$ that equals the inverse of the relaxation time is termed the critical strain rate ($\dot{\varepsilon}_c$) and corresponds to a Weissenberg that is equal to one, Wi=$\dot{\varepsilon}_c\lambda$=1.0, and results in the coil-stretch transition of the polymer in solution. Bird, R. B. et al., 1987, New York: John Wiley & Sons. In these experiments, collagen assembles when Wi exceeds 1.0 because the monomers will be aligned.

Collagen fibrillogenesis rates ($f_t$). Assembly kinetics of collagen are investigated by both optical and rheological methods. Because pH, molecular crowding, and the extensional strain rate are used to trigger assembly, it is important to independently measure the effect of each of these parameters on the kinetics of assembly. The method involves first establishing the baseline kinetics in unstrained microvolumes of collagen solution. Second, systems are selected with promising assembly speed scales, and it is determined if extensional strain enhances the rate of fibrillogenesis.

Microvolume assembly kinetic experiments: Microvolumes of collagen solution at five different concentrations (5 mg/ml, 30 mg/ml, 60 mg/ml, 120 mg/ml, and 240 mg/ml) are deposited under silicone oil or into neutral PEG solution (concentrations 1%, 5%, 10%, 20% and 30%) with a glass micropipette at 25° C. and 37° C.

Assessment: The rate of fibrillogenesis is tracked by DIC microscopy mounted onto, for example, the Nikon TE2000E microscope.

Result: The neutral PEG solution significantly affects the rate of collagen assembly via local molecular crowding and neutralization (proton transport). The rate of collagen assembly against collagen concentration, temperature, PEG concentration and PEG molecular weight is plotted. The rates help determine the collagen concentration, temperature, PEG concentration, and PEG molecular weight to use in the disclosed methods and devices.

Because a high PEG concentration causes very rapid fibrillogenesis, which may make it difficult to observe the kinetics of the process, we inject the collagen into PEG in a space confined between two glass plates and track the fibrillogenesis front movement. The rate of assembly is estimated after correcting for the rate of diffusion as the assembly front moves into the collagen at a rate proportional to the root of the diffusion coefficient of protons. Thus, we extrapolate to find the rate of assembly.

A set extensional strain rate ($\dot{\varepsilon}_c$) to use for fibrillogenesis. As described herein, the microfluidics structure can be cylindrical in addition to a flat substrate. To examine the effect of extensional strain on the assembly kinetics of collagen, we use a custom filament stretching rheometer (FiSER). In these experiments, an initial nearly cylindrical fluid sample is placed between two cylindrical plates and stretched with an exponential velocity to produce constant uniaxial extensional ($\dot{\varepsilon}$) that can be used to determine the relationship between $\dot{\varepsilon}$ and fibrillogenesis. It is known that detecting changes of solution birefringence with polarization microscopy during filament stretching can be accomplished (Bischoff-White, E. and J. P. Rothstein, Rheologica Acta, 2012. 51: p. 303-314; Chellamuthu, M. et al., J. Rheol., 2011. 55: p. 901-920; Rothstein, J. P., J. Rheol., 2003. 47: p. 1227-1247; Rothstein, J. P. and G. H. McKinley, *Inhomogeneous transient uniaxial extensional rheometry*. J. Rheol., 2002. 46: p. 1419-1443; Rothstein, J. P. and G. H. McKinley, J. Non-Newtonian Fluid Mech., 2002. 108: p. 275-290), providing supporting that detecting fibrillogenesis onset can be accomplished.

Method. Small volumes of collagen solution (5 mg/ml, 30 mg/ml, 60 mg/ml, 120 mg/ml and 240 mg/ml) at varying pH values (2, 4, 6, 7.3 or 8) are loaded onto opposing plates at either 25° C. or 37° C. at 100% relative humidity. The plates are separated to produce an extensional strain rate, which we calculate from the shear experiments to be about 20% above, equal to, or below about 20% above the set extensional strain rate ($\dot{\varepsilon}_c$), which produces a Weissenberg number of 1.0 (the value we expect to cause collagen assembly). In some embodiments, the extensional strain rate about 30% above or below the set extensional strain rate; about 40% above or below the set extensional strain rate; about 50% above or below the set extensional strain rate; about 60% above or below the set extensional strain rate; about 70% above or below the set extensional strain rate; about 80% above or below the set extensional strain rate; about 90% above or below the set extensional strain rate; or more.

Assessment. Polarization images and extensional viscosity changes provide a positive indication of polymerization onset. We will examine fibrils produced by the extensional rheometer by X-ray, TEM and SEM.

Result. We determine the extensional strain rate that induces assembly of an organized array of collagen fibrils for each collagen concentration at 25° C. or 37° C. and for different pH values. The data helps to set the initial control for collagen solution concentration, pH, temperature, extensional strain rate, etc. to use for the disclosed methods and devices.

Microfluidics devices. We use the values we determined ($\dot{\varepsilon}_c$, $f_t$, $\mu$) to inform a COMSOL multiphysics model of embodiments of the disclosed devices. Modeling: We use two fluids (for example, PEG and silicone oil) that will co-flow with the prefibrillar collagen solution. The PEG layer is modeled as a non-Newtonian fluid (shear-dependent viscosity determined by us) with an osmotic pressure in excess of the feeder collagen solution (osmotic pressure modeled theoretically for both fluids). The slip layer is modeled as an immiscible fluid with low $\mu$ (found for silicone oil in a materials database). The input parameters are chosen inversely to induce the model to converge on hyperbolic geometries, which generates constant extensional strain rates just below $\dot{\varepsilon}_c$ for a period of time long enough to permit nearly full fibrillogenesis (based on $f_t$).

Result: The model provides a set of design criteria for the disclosed methods and devices. The output values of the model mathematically define the boundaries of the hyperbolic contractor as a function of $\dot{\varepsilon}_c$, $f_t$, and $\mu$)

Example 3

Prototypes of Microfluidics Devices

We build multiple prototype devices based on the parameters that we extract from the multiphysics model described above in Example 2. The devices are tested over the range of parameters predicted by the model to produce the an organized array of collagen fibrils. Multiple assessments of the substructure of the collagen fibrils and lamellae produced are conducted via micro-mechanical testing, X-ray, SEM, TEM and AFM.

These Examples generate embodiments of the disclosed devices and methods that controllably generate nanoscale collagen alignment and organization within structures that are similar in size to the fundamental structural unit found in many connective tissues (for example, fibrils and lamellae). The disclosed devices and methods are used to regenerate the structural complexity of collagen-based tissues de novo.

In some embodiments, the structures generated by the disclosed devices and methods are further conditioned, for example, by addition of should, with further conditioning, for example, by addition of glycosaminoglycans (GAGs), cross-linking agents, and cells, for natural tissue replacement.

Microfluidic chips are from Draper Laboratories. In some embodiments, the micro/nanofluidics chips have aperture resolutions that are less than a micron. Order of magnitude calculations suggest that the smallest dimension of a hyperbolic contractor, designed to produce $\dot{\varepsilon}_c$ for 3 mg/ml collagen, is about 200 microns (outlet channel width). In some embodiments, the microfluidic structure is flat or a cylindrical structure. In some embodiments, the flat microfluidic chip is made of glass on polydimethylsiloxane (PDMS).

Method. The co-flow microfluidic chips are fed with three solutions (in some embodiments, collagen, PEG and silicone oil) at concentrations and flow rates prescribed by our model. Generated fibrils are captured on a small powered spool, which draws the fibrils at a rate equal to or faster than the flow to trip fibrillogenesis at the outlet of the chip (i.e. raise the strain rate to equal to or above the supra $\dot{\varepsilon}_c$).

Assessments. Fibrils are tested for their mechanical strength (as described in Paten, J. A., et al., Biomaterials, 2013. 34(11): p. 2577-87). We examine the gross morphology of the fibrils with DIC imaging and their nanoscale organization using Quick Freeze Deep Etch (QFDE)/SEM and TEM. Determination of their structural arrangement (overall fibril anisotropy and banding pattern) are performed using Dr. Minus's MM007 HM High-brilliance X-Ray source.

Results. The disclosed methods and devices produce collagen fibrils with predictable, controllable and highly-organized collagen structure. Also, because we use the natural self-assembling mechanism already encoded into the collagen molecule, we generate fibrils with the correct native architecture. Our disclosed methods are quantitative and allow high precision process control.

In some embodiments, collagen fibrils anneal into proper organization if they are soaked for a period of time in PBS. (Caves, J. M., et al., J Biomed Mater Res B Appl Biomater, 2010. 93(1): p. 24-38).) In some embodiments, we allow collagen to switch into appropriate orientation given their high rotational diffusion speed using such an annealing period. For example, FIGS. 5A-C was produced after such an annealing period.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of organizing prefibrillar solution into an organized array of fibrils comprising:
providing a collagen and/or elastin solution, wherein the collagen and/or elastin are prefibrils; and
creating a fluid flow through the prefibrillar solution by converging flow produced by hyperbolic contraction of the solution that produces a controlled extensional strain and shear strain to the collagen and/or elastin prefibrils, wherein the extensional and shear strain are sufficient to induce the prefibrils to assemble into an organized array of fibrils.

2. The method of claim 1, wherein the solution further comprises fibronectin and/or proteoglycans.

3. The method of claim 1, wherein a drawing probe generates the extensional strain.

4. The method of claim 1, wherein the solution is in the form of a droplet, sheet, sphere, or cylinder.

5. The method of claim 1, further comprising adding supplemental prefibrils to the solution during application of the strain.

6. The method of claim 1, further comprising continuously extending a fibrillar structure at a rate of about 1 µm/second to about 1 mm/second.

7. The method of claim 1, further comprising extending the organized array of fibrils in the presence of a co-nonsolvency agent.

8. The method of claim 1, further comprising exposing the organized array of fibrils to a solution that promotes recrystallization.

9. The method of claim 8, wherein the solution that promotes recrystallization is a buffer comprising a hypertonic agent.

10. The method of claim 9, wherein the hypertonic agent is polyethylene glycol, hyaluronic acid, or glycosaminoglycans.

11. The method of claim 1, further comprising applying tension to the organized array of fibrils as the fibrils recrystallize.

12. The method of claim 1, wherein the total concentration of the collagen and/or elastin in the prefibrillar solution is about 1.2 mg/ml to about 500 mg/ml.

13. The method of claim 12, wherein the total concentration of the collagen and/or elastin in the prefibrillar solution is about 2.4 mg/ml to about 100 mg/ml.

* * * * *